US012811011B2

(12) United States Patent
Kittel

(10) Patent No.: US 12,811,011 B2
(45) Date of Patent: Nov. 24, 2026

(54) AUTOMATED HEALTH MONITORING SYSTEM AND METHOD

(71) Applicant: INNOVACCER INC., San Francisco, CA (US)

(72) Inventor: Michelle MN Kittel, Coshocton, OH (US)

(73) Assignee: INNOVACCER INC., San Francisco, CA (US)

( * ) Notice: Subject to any disclaimer, the term of this patent is extended or adjusted under 35 U.S.C. 154(b) by 223 days.

(21) Appl. No.: 17/960,565

(22) Filed: Oct. 5, 2022

(65) Prior Publication Data

US 2023/0106257 A1 Apr. 6, 2023

Related U.S. Application Data

(60) Provisional application No. 63/252,862, filed on Oct. 6, 2021.

(51) Int. Cl.
*G16H 50/30* (2018.01)

(52) U.S. Cl.
CPC .................................. *G16H 50/30* (2018.01)

(58) Field of Classification Search
None
See application file for complete search history.

(56) References Cited

U.S. PATENT DOCUMENTS 6,135,966 A * 10/2000 Ko ....................... A61B 5/7267 600/481
6,408,294 B1 6/2002 Getchius ........... G06F 16/24534
6,484,161 B1 11/2002 Chipalkatti ............ G06Q 30/02
7,047,242 B1 5/2006 Ponte ...................... G06Q 10/00
7,611,466 B2 11/2009 Chalana ............... A61B 8/0858
8,515,939 B2 8/2013 Chen et al. ............. G06F 17/30
8,630,878 B1 1/2014 Kravets et al. ........ G06Q 40/08
8,849,693 B1 9/2014 Koyfman ............... G06Q 30/02
8,977,953 B1 3/2015 Pierre ................... G06F 40/284

(Continued)

FOREIGN PATENT DOCUMENTS

CN 109508432 3/2019 ........... G06F 16/955
CN 109871538 6/2019 ............. G06F 17/27

(Continued)

OTHER PUBLICATIONS

Arjona et al. "Triggerflow: Trigger-based orchestration of serverless workflows", Future Generation Computer Systems 124, 2021, pp. 215-229.

(Continued)

*Primary Examiner* — John A Pauls
(74) *Attorney, Agent, or Firm* — Hayes Soloway P.C.

(57) ABSTRACT

Systems and methods are provided herein for determining health threats to an individual and generating health threat assessments for an individual. The systems and methods obtain data-sets and environmental data-sets related to an individual, and the data-sets and environmental data-sets are communicated to a health assessment program. The health assessment program processes the data-sets and environmental data-sets to determine if a health threat is present for the individual. The health assessment program generates a health threat assessment, which may be displayed in readable format on an output device.

16 Claims, 7 Drawing Sheets

(56) References Cited

U.S. PATENT DOCUMENTS 9,292,707 B1 3/2016 Fontecchio ............. G06F 21/60
9,355,273 B2 5/2016 Stevens .................... G06F 21/00
9,542,393 B2 1/2017 Morton ............... G06F 16/7844
9,633,404 B2 4/2017 Chawla et al. ........... G06F 7/04
9,727,591 B1 8/2017 Sharma ................. G06F 16/215
9,830,476 B2 11/2017 Fontecchio ............... H04L 9/32
10,056,078 B1 8/2018 Shepherd .............. G06F 16/632
10,147,504 B1 12/2018 Stettin et al. .......... G16H 50/30
10,366,346 B2 7/2019 Achin et al. ............ G06F 15/18
10,514,949 B1 12/2019 Korda ........................ G06F 9/46
10,642,648 B2 5/2020 Ling et al. ................ G06F 9/48
10,691,976 B2 6/2020 Rogers et al. ........... G06K 9/62
10,789,373 B2 9/2020 Reid et al. .............. G06F 21/60
10,810,223 B2 10/2020 Sundararaman et al. ................... G06F 16/254
10,885,759 B1 * 1/2021 Lee .................... G08B 21/0446
10,887,202 B2 1/2021 Hutchison et al. ..... H04L 12/26
10,910,089 B2 2/2021 Austin et al. ........... G06F 21/62
10,983,843 B2 4/2021 Duggal et al. ............ G06F 9/54
11,474,836 B2 10/2022 Awadallah et al. ..... G06F 9/448
11,670,422 B2 6/2023 Basu et al. ............. G16H 50/70
11,682,041 B1 6/2023 Xu et al. ............ G06Q 30/0201
11,687,940 B2 6/2023 Muthuswamy et al. ..................... G06Q 20/4016
11,783,260 B2 10/2023 Flumara et al. ......... G06N 5/04
2003/0018633 A1 1/2003 Horn ....................... G06F 17/18
2004/0215629 A1 10/2004 Dettinger ............ G06F 16/2452
2005/0065956 A1 3/2005 Brown .................. G06F 16/252
2005/0107902 A1 5/2005 Blouin ................. G06Q 10/087
2005/0119534 A1 6/2005 Trost ....................... G06F 19/00
2005/0131778 A1 6/2005 Bennett .............. G06Q 10/0875
2006/0041539 A1 2/2006 Matchett ............ G06Q 10/0639
2006/0075001 A1 4/2006 Canning ................... G06F 8/65
2007/0239694 A1 10/2007 Singh et al. .............. G06F 7/00
2007/0239724 A1 10/2007 Ramer .................. G06F 16/951
2008/0147554 A1 6/2008 Stevens et al. ........... H04L 9/00
2008/0263187 A1 10/2008 Casey et al. .......... G06F 15/173
2009/0012818 A1 1/2009 Rodgers ................. G16H 10/65
2009/0112114 A1 4/2009 Ayyagari et al. ........ A61B 5/08
2009/0313232 A1 12/2009 Tinsley .................. G06Q 30/02
2010/0121879 A1 5/2010 Greenberg ............ G06F 16/248
2010/0199169 A1 8/2010 Gnech ................... G06F 16/972
2010/0287162 A1 11/2010 Shirwadkar ......... G06F 16/3338
2011/0082712 A1 4/2011 Eberhardt, III et al. ................... G16Z 99/00
2012/0083933 A1 * 4/2012 Subbu ...................... G06N 3/02 700/291
2012/0253793 A1 10/2012 Ghannam ............... G06F 17/27
2013/0054010 A1 2/2013 Holman et al. ........ G06Q 50/01
2013/0054625 A1 2/2013 Bhagwan et al. ..... G16H 10/60
2013/0054695 A1 2/2013 Holman et al. ........ G09B 19/00
2013/0197936 A1 8/2013 Willlich ................. G06Q 50/22
2013/0246290 A1 9/2013 Courson et al. ...... G06F 40/205
2013/0325805 A1 12/2013 Tochilnik ................ G06F 17/30
2014/0006061 A1 1/2014 Watanabe .............. G06Q 30/02
2014/0107932 A1 * 4/2014 Luna ...................... G16H 50/20 702/19
2014/0149446 A1 5/2014 Kuchmann-Beauger .................... G06F 17/30389
2014/0156315 A1 6/2014 Canovi et al. ......... G06Q 40/08
2014/0188835 A1 7/2014 Zhang ................. G06F 17/2705
2014/0344261 A1 11/2014 Navta ................... G06F 16/951
2014/0350954 A1 11/2014 Ellis et al. ............. G16H 10/60
2015/0088786 A1 * 3/2015 Anandhakrishnan .. G16H 50/80 706/11
2015/0127379 A1 5/2015 Sorenson ................ G06F 19/00
2015/0142807 A1 5/2015 Hoffman et al. ........ G06N 3/02
2015/0164430 A1 6/2015 Hu ....................... A61B 5/7264
2015/0302529 A1 10/2015 Jagannathan .......... G06Q 40/08
2015/0363478 A1 12/2015 Haynes ................... G06F 16/26
2016/0085915 A1 3/2016 Seow ...................... G06F 19/00
2016/0098387 A1 4/2016 Bruno ..................... G06F 17/27
2016/0132969 A1 5/2016 Gunjan et al. ......... G06Q 40/08
2016/0147945 A1 5/2016 MacCarthy et al. .... G06F 19/00
2016/0156611 A1 6/2016 Rozman .................. H04L 29/06
2016/0162473 A1 6/2016 Cogley ................... G06F 40/51
2016/0371453 A1 12/2016 Bowman ................. G06F 19/00
2016/0373456 A1 12/2016 Vermeulen .............. G06F 16/25
2017/0076046 A1 3/2017 Barnes et al. .......... G06F 19/00
2017/0091162 A1 3/2017 Emanuel ............... G06F 40/169
2017/0102693 A1 4/2017 Kidd ................ G05B 19/41865
2017/0161372 A1 6/2017 Fernandez .............. G06F 16/35
2017/0199928 A1 7/2017 Zhao ................. G06F 16/24578
2017/0256173 A1 9/2017 Burford ................. G09B 5/125
2017/0277853 A1 * 9/2017 Carlson .................. G16H 50/30
2017/0279786 A1 9/2017 Peterson et al. ........ H04L 29/06
2017/0323485 A1 11/2017 Samec et al. ........... G06T 19/00
2017/0337326 A1 11/2017 Zhang et al. ........... G06F 19/24
2017/0344646 A1 11/2017 Antonopoulos ........ H04L 9/008
2017/0364637 A1 12/2017 Kshepakaran et al. ...................... G06F 19/00
2017/0371881 A1 12/2017 Reynolds .............. G06F 16/248
2018/0025122 A1 1/2018 Schuurkamp et al. . G06F 19/00
2018/0033279 A1 * 2/2018 Chong ............... G06Q 10/0633
2018/0052842 A1 2/2018 Hewavitharana et al. .................. G06F 17/3043
2018/0113986 A1 4/2018 Zhu ..................... G06F 19/3418
2018/0158146 A1 6/2018 Turner ................... G06Q 40/02
2018/0158551 A1 6/2018 Bradley et al. ........ G16H 40/67
2018/0168464 A1 * 6/2018 Barnett, Jr. .......... A61B 5/6861
2018/0173733 A1 6/2018 Nath et al. .............. G06F 17/30
2018/0203978 A1 7/2018 Basu et al. ............. G16H 50/30
2018/0210925 A1 * 7/2018 Raghavan ............... G06F 17/18
2018/0225320 A1 8/2018 Saini ..................... G06F 16/215
2018/0232443 A1 8/2018 Delgo .................... G06Q 30/06
2018/0367557 A1 12/2018 Brown ................ H04L 63/1425
2019/0012390 A1 1/2019 Nishant .................. G06N 20/00
2019/0013093 A1 1/2019 Slepian et al. ......... G16H 40/20
2019/0050445 A1 2/2019 Griffith ................ G06K 9/6262
2019/0114511 A1 4/2019 Gao et al. ................ G06K 9/62
2019/0156198 A1 5/2019 Mars ...................... G06N 20/20
2019/0179820 A1 6/2019 El Kaed ............. G06F 16/2471
2019/0180757 A1 6/2019 Kothari ................. G10L 17/005
2019/0244129 A1 8/2019 Tabuchi et al. ....... G06F 9/5033
2019/0259108 A1 8/2019 Bongartz et al. ...... G06Q 50/02
2019/0304582 A1 10/2019 Blumenthal et al. .. G16H 15/00
2019/0311299 A1 10/2019 Lindner ................ G06F 16/248
2019/0311300 A1 10/2019 Lindner ................. G06N 20/00
2019/0311372 A1 10/2019 Lindner ................. G06N 20/00
2019/0318272 A1 10/2019 Sassin .................. G06N 99/005
2019/0324964 A1 10/2019 Shiran .................... G06N 20/00
2020/0004749 A1 1/2020 Slezak ................ G06F 16/2462
2020/0067789 A1 2/2020 Khuti et al. ............ H04L 41/16
2020/0074461 A1 3/2020 DeRosa-Grund ...... G06Q 20/38
2020/0092099 A1 3/2020 Austin et al. ............. H01L 9/14
2020/0117434 A1 4/2020 Biskup et al. ............ G06F 8/60
2020/0160955 A1 5/2020 Hansen et al. ......... G16H 15/00
2020/0175028 A1 6/2020 Kozlowski et al. .. G06F 16/252
2020/0211692 A1 7/2020 Kalafut et al. ......... G16H 30/20
2020/0257611 A1 8/2020 Hortala et al. .......... G06F 11/36
2020/0294642 A1 9/2020 Bostic et al. .......... G16H 50/20
2020/0303075 A1 * 9/2020 Krishna ................. G16H 50/30
2020/0387623 A1 12/2020 Bayon et al. ....... G06F 21/6227
2021/0090694 A1 3/2021 Colley et al. .......... G16H 10/60
2021/0174135 A1 6/2021 Liu et al. ................. G06K 9/62
2021/0272696 A1 9/2021 DeMazumder ........ G16H 15/00
2021/0287656 A1 9/2021 Bonafonte et al. ..... G10L 13/10
2021/0319796 A1 10/2021 Wang et al. ............ G10L 15/26
2021/0374143 A1 12/2021 Neill ................. G06F 16/24568
2021/0398024 A1 12/2021 Pargunarajan et al. ...................... G06N 20/00
2022/0004443 A1 1/2022 Duggal et al. ............ G06F 9/54
2022/0075772 A1 3/2022 Korpman et al. .. G06F 16/9024
2022/0121651 A1 4/2022 Korpman et al. ...... G06F 16/23
2022/0164337 A1 5/2022 Korpman et al. .... G06F 40/205
2022/0180985 A1 6/2022 Connely, IV et al. . G16H 10/60
2022/0215948 A1 7/2022 Bardot ................... G16H 40/40
2022/0262517 A1 * 8/2022 Van Sickle ....... H02J 13/00001
2022/0269732 A1 8/2022 Pange et al. .......... G06F 9/3555
2022/0374631 A1 11/2022 Gao et al. ................ G06K 9/00
2022/0399112 A1 12/2022 Bardot ................... G16H 40/40
2023/0087478 A1 3/2023 Jayaram et al. .... G06F 16/2365
2023/0119881 A1 4/2023 Makhija et al. . G06V 30/19147

(56) References Cited

U.S. PATENT DOCUMENTS

| | | | | |
|---|---|---|---|---|
| 2023/0123620 | A1 | 4/2023 | Simpson | G06F 3/0482 |
| 2023/0139172 | A1 | 5/2023 | Booth et al. | G16H 10/60 |
| 2023/0142594 | A1 | 5/2023 | Eberhardt et al. | G16H 50/20 |
| 2023/0153722 | A1 | 5/2023 | Simpson | G06Q 40/04 |
| 2023/0207126 | A1 | 6/2023 | Molero Leon et al. | G06N 20/00 |
| 2023/0229999 | A1 | 7/2023 | Fowles et al. | G06Q 10/063 |
| 2023/0252020 | A1 | 8/2023 | Korpman et al. | G06F 16/9027 |
| 2023/0252382 | A1 | 8/2023 | Simpson | G06Q 50/02 |
| 2023/0260045 | A1 | 8/2023 | Nawab et al. | G06V 10/82 |
| 2023/0262118 | A1 | 8/2023 | Jayaram et al. | G06Q 40/06 |
| 2023/0281546 | A1 | 9/2023 | Markison | G06F 18/241 |
| 2023/0325894 | A1 | 10/2023 | Nilekar | G06Q 30/0601 |
| 2023/0326568 | A1 | 10/2023 | Greebel et al. | G16H 50/70 |
| 2023/0326577 | A1 | 10/2023 | Prince et al. | |
| 2023/0350901 | A1 | 11/2023 | Neill | G06F 16/24568 |
| 2023/0376532 | A1 | 11/2023 | McCarthy et al. | G06F 16/84 |
| 2023/0409966 | A1 | 12/2023 | Lindner | G06F 16/248 |

FOREIGN PATENT DOCUMENTS

| | | | |
|---|---|---|---|
| CN | 110245676 | 9/2019 | G06K 9/62 |
| CN | 110998532 | 4/2020 | G06F 9/50 |
| CN | 112262368 | 1/2021 | G06F 8/30 |
| CN | 113420541 | 9/2021 | |
| CN | 116434951 | 7/2023 | |
| CN | 118246439 | 6/2024 | |
| JP | 2004-318565 | 11/2004 | G06F 17/60 |
| KR | 10-1999152 | 7/2019 | G06F 17/27 |
| WO | WO-2012023136 A1 * | 2/2012 | G01N 33/00 |
| WO | WO 2012/051389 | 4/2012 | G06F 7/00 |
| WO | WO 2017/161403 | 9/2017 | G06Q 30/02 |
| WO | WO 2018/057647 | 3/2018 | C12Q 1/68 |
| WO | WO 2018/166853 | 9/2018 | G16H 10/60 |
| WO | WO/2020150228 | 7/2020 | G16H 10/60 |
| WO | WO 2020/219971 | 10/2020 | G06N 3/04 |
| WO | WO 2021/036070 | 3/2021 | G06F 16/22 |

OTHER PUBLICATIONS

Carver et al. "In Search of a Fast and Efficient Serverless DAG Engine", George Mason University, Nov. 18, 2019, 10 pgs.
International Search Report and Written Opinion issued in PCT/US2023/021014, dated Jul. 28, 2023, 9 pgs.
Datavant—Connecting the world's health data, slide presentation, https://www.healthra.org/wp-content/uploads/2018/10/Datavant-Overivew-Deck_Prepared-for-HRA_v20181002-1.pdf Oct. 2018, 15 pgs.
"De-identification and re-identification of PII in large-scale datasets using Cloud DLP", Cloud Architecture Center, https://cloud.google.com/architecture/de-identification-re-identification-pii-using-cloud-dlp, Aug. 11, 2022, 9 pgs.
Shin, "Encoding Database Schemas with Relation-Aware Self-Attention for Text-to-SQL Parsers", arXiv: 1906.11790v1 [cs.LG] Jun. 27, 2019, 10 pgs.
Suleiman et al., "Deep Learning Based Abstractive Text Summarization: Approaches, Datasets, Evaluation Measures, and Challenges", Hindawi, Mathematical Problems in Engineering, vol. 2020, Article ID 9365340, Aug. 24, 2020, 29 pgs.
International Search Report and Written Opinion issued in PCT/2022/045784, dated Feb. 8, 2023, 10 pgs.
International Search Report and Written Opinion issued in PCT/US20/13802 dated Mar. 25, 2020 (10 pgs).
International Search Report and Written Opinion issued in PCT/US20/16827 dated Apr. 22, 2020 (7 pgs).
International Preliminary Report on Patentability issued in PCT/US2020/013802, dated Aug. 10, 2021, 7 pgs.
International Preliminary Report on Patentability issued in PCT/US2020/016827, dated Aug. 10, 2021, 5 pgs.
EPO Supplementary Search Report issued in EP20754922.1, dated Oct. 4, 2022, 12 pgs.
Notice of Allowance issued in U.S. Appl. No. 16/387,016, dated Feb. 10, 2020 (14 pgs).
Notice of Allowance issued in U.S. Appl. No. 16/363,897, dated Jul. 30 2020 (18 pgs).
Notice of Allowance issued in U.S. Appl. No. 16/743,175, dated Jul. 31, 2020 (18 pgs).
Office Action issued in U.S. Appl. No. 16/387,016, dated Jun. 25, 2019 (11 pgs).
Office Action issued in U.S. Appl. No. 16/387,016, dated Oct. 17, 2019 (17 pgs).
Office Action issued in U.S. Appl. No. 16/363,897, dated Sep. 9, 2019 (38 pgs).
Office Action issued in U.S. Appl. No. 16/363,897, dated Feb. 26, 2020 (36 pgs).
Office Action issued in U.S. Appl. No. 16/743,175 dated Mar. 23, 2020 (21 pgs).
Office Action issued in India Application No. 201921043365, dated Dec. 10, 2021, 7 pgs.
Morid et al. "Supervised Learning Methods for Predicting Healthcare Costs: Systematic Literature Review and Empirical Evaluation", 2018, AMIA Annu Symp Proc. pp. 1312-1321.
Wang et al. "Detecting Transportation Modes Based on LightBGM Classifier from GPS Trajectory Data", 2018 26$^{th}$ International Conference on Geoinformatics, Kunming, 2018, pp. 1-7.
Zhang et al. "Health reform and out-of-pocket payments: lessens from China", Health Policy and Planning, vol. 29, Issue 2, Mar. 2014, pp. 217-226, https://doi.org/10.1093/heapol/czt006.
Iyengar et al. "A Trusted Healthcare Data Analytics Cloud Platform", 2018 IEEE 38$^{th}$ International Conference on Distributed Computing Systems (ICDCS), Vienna, 2018, pp. 1238-1249.
U.S. Appl. No. 18/540,583, filed Dec. 14, 2023, Lakshman et al.
International Search Report and Written Opinion issued in PCT/US2023/025897, dated Sep. 21, 2023, 10 pgs.
International Search Report and Written Opinion issued in PCT/US2022/050117 dated Mar. 3, 2023 (8 pgs).
International Search Report and Written Opinion issued in PCT/US2022/050616 dated Mar. 27, 2023 (7 pgs).
"Artificial Intelligence for the Data-Driven Enterprise" *Informatica*, informatica.com, 2023, 36 pages.
Gill, Navdeep Singh "Big Data Ingestion Tools and its Architecture | The Advanced Guide" Xenonstack a Stack Innovator, Apr. 29, 2023, https://www.xenonstack.com/blog/big-data-ingestion, 16 pages.
He et al., "The practical implementation of artificial intelligence technologies in medicine" *Nat Med*, Jan. 2019; 25(1):30-36, 15 pages.
Kaur et al., "AI based HealthCare Platform for Real Time, Predictive and Prescriptive Analytics using Reactive Programming" *Journal of Physics: Conference Series* 933 (2018), 13 pages.
Krugman, Brandon, "Converting Medical Service Provider Data into a Unified Format for Processing" (2015).*Master's Theses* (2009 -). Paper 322. http://epublications.marquette.edu/theses_open/322, 50 pages.
U.S. Appl. No. 17/988,505, filed Nov. 16, 2022, Gupta et al.
U.S. Appl. No. 17/991,554, filed Nov. 21, 2022, Kumar et al.
U.S. Appl. No. 18/212,562, filed Jun. 21, 2023, Singh.
U.S. Appl. No. 18/143,397, filed May 4, 2023, Gupta et al.
U.S. Appl. No. 18/40,434, filed Jan. 23, 2024, Raghuvansh et al.
Notice of Allowance issued in U.S. Appl. No. 17/991,554, dated Sep. 26, 2024, 9 pgs.
Wilson et al., "Case-Based Decision Support for Intelligent Patient Knowledge Management", 3$^{rd}$ Intl. IEEE Conference, Sep. 2006, 6 pgs.
Chen et al., "Learning Semantic Annotations for Tabular Data", Proceedings of the Twenty-Eighth International Joint Conference on Artificial Intelligence (IJCAI-19), Aug. 2019, 7 pgs.
Gorman et al., "Structured Abbreviation Expansion in Context", arXiv:2110.01140v1 [cs.CL] Oct. 2021, 11 pgs.
Ratinov et al., "Abbreviation Expansion in Schema Matching and Web Integration", Proceedings of the IEEE/WIC/ACM International Conference on Web Intelligence (WI'04), 2004, 5 pgs.

(56) References Cited

OTHER PUBLICATIONS

Xu et al., "Modeling Tabular Data using Conditional GAN", 33rd Conference on Neural Information Processing Systems (NeurIPS 2019), Vancouver, Canada, 11 pgs.

* cited by examiner

AUTOMATED HEALTH MONITORING SYSTEM AND METHOD

CROSS REFERENCE TO RELATED APPLICATION

This application claims benefit of U.S. Provisional Application Ser. No. 63/252,862 entitled, "Automated Health Monitoring System and Method" filed Oct. 6, 2021, the entire disclosure of which is incorporated herein by reference.

TECHNICAL FIELD

The present disclosure relates to processes for monitoring the health of an individual, and more particularly to automated systems and processes for identifying and notifying individuals of risks to an individual's health.

BACKGROUND

Over the past decades, average life expectancies of individuals have increased, in part due to advances in medical science and technology. Consequently, elderly populations world-wide have been increasing, and with this increase research and development of health monitoring applications have risen as well. Elderly populations, on average, tend to suffer in greater numbers from chronic health conditions that put their health and lives at risk, such as cardiovascular diseases, cancers, respiratory illnesses, and so on.

Health monitoring applications, however, generally focus on acute health conditions of individuals, and fail to account for external factors that can impact individuals, particularly individuals suffering from chronic health conditions. Accordingly, unaddressed needs exist for improving health monitoring applications to improve health monitoring for many individuals and for populations of individuals.

SUMMARY

Shortcomings of the prior art are overcome and additional advantages are provided through the provision, in one aspect, of a method. The method includes obtaining one or more data-sets for one or more physical or physiological parameters associated with an individual, and obtaining one or more environmental data-sets for one or more environmental parameters associated with a location of the individual. The method further includes communicating the one or more data-sets and the one or more environmental data-sets to a health assessment program, wherein the health assessment program comprising instructions to determine one or more health threats to the individual. The method further includes processing the one or more data-sets and the one or more environmental data-sets using the health assessment program to determine if one or more health threats to the individual are present, and generating a health threat assessment related to the individual based on the one or more data-sets and the one or more environmental data-sets. The method further includes communicating the health threat assessment to an output device, the output device configured to output the health threat assessment in readable format to the individual, and displaying the health threat assessment via the output device.

In one embodiment, obtaining the one or more environmental data-sets includes obtaining, via one or more environmental sensors, the one or more environmental data-sets associated with the location of the individual. In another embodiment, obtaining the one or more environmental data-sets includes obtaining, via a cloud computing node, the one or more environmental data-sets associated with the location of the individual. In various embodiments, the one or more environmental parameters associated with the location of the individual includes one or more of: a temperature; an internal temperature; an oxygen level; a humidity level; a barometric pressure.

In embodiments, obtaining the one or more data-sets includes obtaining, via one or more medical sensors, one or more physical or physiological parameters associated with an individual. In various embodiments the one or more data-sets associated with the individual includes one or more of: a heart-rate; a respiratory rate; a blood pressure; an oxygen saturation level; a blood sugar level; a temperature; fertility; a ketone level.

In embodiments, the method further includes generating, via an alert generation program, one or more alerts responsive to the generating the health threat assessment, with the one or more alerts including at least one of an audio alert or visual alert, and playing or displaying the one or more alerts via the output device. In embodiments the output device is a first output device, and the method further includes transmitting at least one alert of the one or more alerts to a second output device, where the second output device is configured to receive the at least one alert, and playing or displaying the at least one alert via the second output device.

In further embodiments, the method further includes obtaining one or more medical condition data-sets, and communicating the one or more medical condition data-sets to the health assessment program. The method further includes processing the one or more medical condition data-sets with the one or more data-sets and the one or more environmental data-sets using the health assessment program to determine if one or more health threats to the individual are present. The method generates the health threat assessment related to the individual based on the one or more data-sets, the one or more medical condition data-sets, and the one or more environmental data-sets. In various embodiments, the one or more medical condition data-sets includes one or data for one or more of the following: a medical history of the individual; medical records of the individual; a medical condition or disease pertaining to the individual; information regarding remedial care for a medical condition or disease pertaining to the individual.

In further embodiments, the method may include, prior to processing the one or more medical condition data-sets with the one or more data-sets, one or more pre-preprocessing steps. The method may include pre-processing the one or more data-sets and the one or more medical condition data-sets to remove inconsistencies from the data of the one or more data-sets and the data of the one or more medical condition data-sets. The method may include pre-processing the one or more data-sets and the one or more medical condition data-sets to assign one or more weight factors to one or more parameters of the one or more data-sets or the one or more medical condition data-sets. The method may further include, prior to generating the health threat assessment, generating a first processed data-set and a second processed data-set, wherein the first processed data-set is used to generate the health threat assessment, and wherein the second processed data-set is stored as a static data-set.

In embodiments the methods may further include communicating the second processed data-set to a computer program, where the computer program is configured to store the second processed data-set with one or more additional processed data-sets for other individuals, and generating a report, based on the second processed data-set and the one or more additional processed data-sets, pertaining to one or more health threats to a population of individuals.

In another aspect a system is provided. The system includes a memory, one or more processing apparatus in communication with the memory, a computer readable storage medium, and one or more programs comprising program instructions stored on the computer readable storage medium and executable by the one or more processing apparatus via the memory to perform a method. The method includes obtaining one or more data-sets for one or more physical or physiological parameters associated with an individual, and obtaining one or more environmental data-sets for one or more environmental parameters associated with a location of the individual. The method further includes communicating the one or more data-sets and the one or more environmental data-sets to a health assessment program, wherein the health assessment program comprising instructions to determine one or more health threats to the individual. The method further includes processing the one or more data-sets and the one or more environmental data-sets using the health assessment program to determine if one or more health threats to the individual are present, and generating a health threat assessment related to the individual based on the one or more data-sets and the one or more environmental data-sets. The method further includes communicating the health threat assessment to an output device, the output device configured to output the health threat assessment in readable format to the individual, and displaying the health threat assessment via the output device.

In embodiments, the system may further include one or more environmental sensors in communication with the processing apparatus, and the method may include obtaining one or more environmental data-sets via the one or more environmental sensors, wherein the one or more environmental data-sets associated with the location of the individual. In embodiments, the system may further include a cloud computing system, with the cloud computing system including one or more cloud computing nodes in communication with the system, and the method may include obtaining one or more environmental data-sets via the cloud computing system, wherein the one or more environmental data-sets associated with the location of the individual.

In embodiments, the system may further include one or more medical sensors connected to or in communication with the system, and the method may include obtaining the one or more data-sets via the one or more medical sensors, including the one or more physical or physiological parameters associated with an individual.

In additional embodiments of the system, the method may include generating, via an alert generation program, one or more alerts responsive to the generating the health threat assessment, wherein the one or more alerts includes at least one of an audio alert or visual alert, and playing or displaying the one or more alerts via the output device. In further embodiments the output device may be a first output device and the system may include a second output device, and the method may further include transmitting at least one alert of the one or more alerts to a second output device, with the second output device configured to receive the at least one alert, and playing or displaying the at least one alert via the second output device.

In yet further embodiments, the system and method may further include obtaining one or more medical condition data-sets, communicating the one or more medical condition data-sets to the health assessment program, and processing the one or more medical condition data-sets with the one or more data-sets to generate the health threat assessment. In further embodiments, the one or more programs of the system may include a pre-processing program, and the method further includes, prior to processing the one or more medical condition data-sets with the one or more data-sets: via the pre-processing program, pre-processing the one or more data-sets and the one or more medical condition data-sets to remove inconsistencies from the data of the one or more data-sets and the data of the one or more medical condition data-sets; via the pre-processing program, pre-processing the one or more data-sets and the one or more medical condition data-sets to assign one or more weight factors to one or more parameters of the one or more data-sets or the one or more medical condition data-sets; and, prior to generating the health threat assessment, generating a first processed data-set and a second processed data-set, wherein the first processed data-set is used to generate the health threat assessment, and wherein the second processed data-set is stored as a static data-set.

Additional features and advantages are realized through the techniques set forth herein. Other embodiments and aspects are described in detail herein and are considered a part of the claimed disclosure.

BRIEF DESCRIPTION OF THE DRAWINGS

One or more aspects of the present disclosure are particularly pointed out and distinctly claimed in the claims at the conclusion of the specification. The foregoing and other objects, features, and advantages as set forth herein are apparent from the following detailed description taken in conjunction with the accompanying drawings in which:

DETAILED DESCRIPTION

Figure 1:
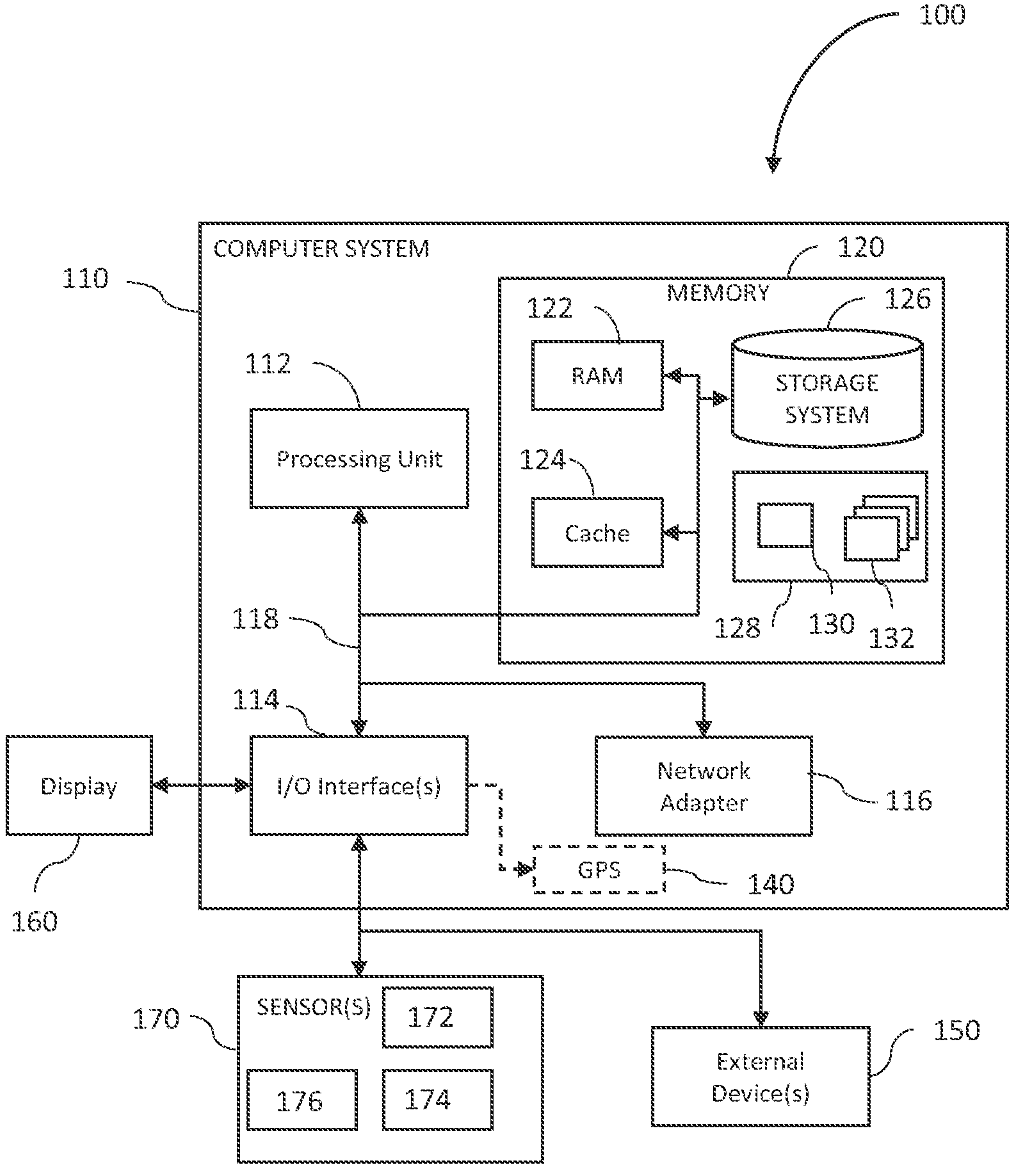
FIG. 1 depicts a system in accordance with one or more embodiments set forth herein.

Aspects of the present disclosure and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the disclosure in detail. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Health monitoring systems may be used in a wide variety of contexts and settings for real-time analysis of health-related data associated with an individual. Health monitoring systems that may be used outside of an inpatient or hospital setting have become more prominent in recent years due to aging populations increasing in size as life expectancy has risen, and individuals increasingly need to monitor their own health data and status to determine if or when risks to their health are present or may manifest in the near future. For example, individuals with diabetes may use a device configured to measure their blood sugar levels to determine if they are at risk for ketoacidosis; similarly, individuals diagnosed with high blood pressure or recovering from a heat attack may use blood-pressure monitors to keep track of their blood pressure and determine if they are at risk for another heart attack or other cardio-vascular complications.

Health monitoring systems generally provide health-related data related to particular bodily functions of an individual. However, such data on its own usually cannot provide a complete assessment of immediate or future risks to an individual's health condition; many external conditions, such as socio-economic conditions or housing and living conditions, may also contribute to the health risks to an individual. It is known that a high degree of correlation between environmental conditions and health conditions exists, such that health conditions that present a relatively low health risk to an individual in normal environmental conditions may be exacerbated by more extreme environmental conditions, putting the individual at greater risk for health complications. For example, it is well understood that elevated heat and humidity can put individuals with high blood pressure at higher risk for cardiac issues, such as stroke or heart attack.

Embodiments of the processes and systems presented herein address these issues and provide individuals with means for receiving health threat assessments that are based on data-sets regarding environmental conditions and data related to an individual's location as well as physical or physiological conditions that are associated with the individual. The health threat assessment may be generated by a health assessment program that contains instructions for determining if one or more health threats exist. The health threat assessment may be delivered through any type of output device, for example a mobile device such as a smartphone, tablet, or wearable electronic device. The health threat assessment may be presented, in some embodiments, through a graphically visualized end-user or client application that can be accessed with the output device. In some embodiments the health threat assessment may automatically generate audio or visual alarms intended to alert an individual to present or anticipated health threats, and may, in further embodiments, provide the individual with additional information related to or generated by the health threat assessment, such as remedial guidelines or precautions to ameliorate or eliminate health threats, prompts to take certain medications, and so on. In some embodiments, the alerts may be sent to another or additional devices, such as devices used by an individual's family members or healthcare professionals, to alert others to the health threat to the individual.

In some embodiments, environmental data-sets may be obtained from one or more environmental sensors that are operatively connected or in communication with the output device, so that the environmental data-sets may be used by the health assessment program. The environmental sensors may be configured to collect data-sets regarding, for example, humidity, temperature, oxygen levels, pollen count, pollution levels, and the like. In some embodiments, environmental data-sets may be obtained via a cloud computing node that is capable of transmitting environmental data-sets to the health assessment program. In ideal embodiments, regardless of the source or sources of the environmental data-sets, the obtained environmental data-sets are related to the individual's location. In any embodiments, the obtained environmental data-sets may be communicated to the health assessment program to generate a health threat assessment.

Reference is made below to the drawings, which are not drawn to scale for ease of understanding, wherein the same reference numbers used throughout different figures designate the same or similar components.

FIG. 1 depicts a system 100 that includes a computer system 110, which is operational with numerous other general purpose or special purpose computing system environments or configurations. Examples of well-known computing systems, environments, and/or configurations that may be suitable for use with computer system 110 include, but are not limited to, personal computer systems, server computer systems, thin clients, thick clients, hand-held or laptop devices, multiprocessor systems, microprocessor-based systems, set top boxes, mobile devices such as a mobile phone or tablet, programmable consumer electronics, network PCs, minicomputer systems, mainframe computer systems, and distributed cloud computing environments and/or cloud computing nodes that include any of the above systems or devices, and the like. As described further herein, in exemplary embodiments computer system 110 may be an output device configured to output a health threat assessment in readable format to an individual. Such an output device may be, by way of example and not limitation, a mobile phone device, a mobile tablet device, a personal desktop or laptop computer, or other device capable of outputting and displaying a health threat assessment. In other exemplary embodiments, the output device may be a computer or similar device configured as a dedicated health threat assessment output device. Other output devices are possible and contemplated within the scope of the present disclosure.

As shown in FIG. 1, computer system 110 in system 100 is shown in the form of a general-purpose computing device. The components of computer system 110 may include, but are not limited to, one or more processors or processing units 112, one or more Input/Output (I/O) interfaces 114, one or more network adapters 116, a system memory 120, and a bus 118 that couples various system components including system memory 120 to processing units 112 and other system components.

System memory 120 can include computer system readable media in the form of temporary or volatile memory, such as random access memory (RAM) 122 and/or cache memory 124. Computer system 110 may further include other removable/non-removable, volatile/non-volatile computer system storage media. By way of example only, storage system 126 can be provided for reading from and writing to a non-removable, non-volatile media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided.

In such instances, each can be connected to bus 118 by one or more data media interfaces. In embodiments, storage system 126 may store one or more data-sets for physical or physiological parameters related to an individual, and storage system 126 may be configured to permit one or more program 128, including health assessment program 130, to access and/or update the one or more data-sets.

Storage system 126 may be useful for supporting various types of software applications, such as artificial intelligence ("AI") applications, database applications, electronic design automation tools, event-driven software applications, high performance computing programs, simulation applications, high-speed data capture and analysis programs, machine learning applications, media production applications, media serving applications, picture archiving and communication systems ("PACS") applications, software development applications, virtual reality applications, augmented reality applications, and many other types of applications by providing storage resources to such applications. Artificial intelligence applications and machine learning applications may perform various types of data analysis to automate analytical model building. Using algorithms that iteratively learn from data, artificial intelligence applications and machine learning applications can enable computers to learn without being explicitly programmed. In embodiments described herein, one or more programs 128 may include one or more artificial intelligence applications and/or machine learning applications; further, an artificial intelligence application or machine learning application may be one or more components of any of the one or more programs 128, including health assessment program 130.

Artificial intelligence applications and machine learning applications are modeled on "deep learning" computer models. Deep learning is a computing model that makes use of massively parallel neural networks inspired by the human brain. Instead of an individual programmer or numerous programmers working by hand to build software, an artificial intelligence application or machine learning application built around the deep learning model writes its own software by learning from lots of examples.

A full scale artificial intelligence or machine learning application deployment may be required to continuously collect, clean, transform, label, and store large amounts of data. Adding additional high quality data points directly translates to more accurate models and better insights. Data samples may undergo a series of processing steps including, but not limited to: 1) ingesting the data from an external source into the training system and storing the data in raw form, 2) cleaning and transforming the data in a format convenient for training, including linking data samples to the appropriate label, 3) exploring parameters and models, quickly testing with a smaller dataset, and iterating to converge on the most promising models to push into the production cluster, 4) executing training phases to select random batches of input data, including both new and older samples, and feeding those into computing system for computation to update model parameters, and 5) evaluating including using a holdback portion of the data not used in training in order to evaluate model accuracy on the holdout data. Readers will appreciate that a single shared storage data hub creates a coordination point throughout the lifecycle without the need for extra data copies among the ingest, preprocessing, and training stages. Rarely is the ingested data used for only one purpose, and shared storage gives the flexibility to train multiple different models or apply traditional analytics to the data.

In an embodiment, the back-end server 126 further includes a data repository connected to a plurality of disease information sources and comprising a plurality of data-sets pertaining to disease threat information for various chronic diseases. The plurality of data-sets generally includes the medical history of the patient as well as current records of the monitored parameters, which in turn plays a central role in the emergency response and hospital monitoring system to correlate the data collected from the sensors 170 to the stored thresholds for the parametric values within data-sets. Further, such a correlation is employed by the health assessment module 130 to determine and/or declare a state of emergency for the user. In an embodiment, the data repository may include remedial databases comprising a plurality of remedial data sets including but not limited to a plurality disease related parameters and/or features dataset, health assessment reports comprising assessments of disease/symptoms within the user, remedial and/or treatment dataset comprising suggested recommendations and/or lifestyle plan for avoiding deterioration of health of the user. The data sets comprise historical database from a plurality of users of different age, demographic regions, races, origin, socio-economic, biological considerations, and various other similar variations. In some embodiments, the remedial data-sets may be collected from the external sources, such as health care providers and research institutes, and/or the clinical data accumulated by the public health recovery institutes.

The data repository including the remedial database and the plurality of data-sets are constantly upgraded on the basis of one or more learning models selected from but not limited to Natural language processing (NLP), Deep Learning, Machine Learning, statistical learning model, and the like.

The back-end server 126 further includes a health assessment module 130 adapted to assess health/symptoms of the user of the computing unit 110. Particularly, the health assessment module 130 is configured to process the received data sets in accordance with one or more programming instructions corresponding to a disease rule engine defined by a threat rule-set, so as to determine a possible infection threat, using the received data-sets, and the disease related information data-sets in accordance with the threat rule-set.

The set of programming instructions is generally based on one or more deep learning models and is configured to cause the back-end server 126 and/or the computing unit 110 to assess any possible threats of health hazard and/or infection to the user on the basis of captured environmental and/or medical factors by the one or more of plurality of data sensors 170. In an embodiment of the present invention, the system 100 includes the programming instructions and the implementation to process the data-sets and/or the data repository are based on a deep learning model wherein the model is particularly applied to upgrade the data repository including each of the data sets.

Particularly, the deep learning model includes number of pre-processing steps that are applied on the data stored in all the individual data sets. The pre-processing steps may include cleansing the data to remove any inconsistencies and assigning weights to each of the parameter for consideration of assessments. Particularly, a list of parameters/features may be determined at this step.

Further, the machine learning model and/or the deep learning model includes a learning engine adapted to run a selected model (e.g., deep learning model, Random Forest, multi linear regression, Multilayered, feed-forward neural networks, statistical model or the like) on the data sets, and partitions them into either a training dataset or a testing dataset. In a preferred embodiment, the partitioning may apply an 80/20 split between the training dataset and the testing dataset, respectively.

Thereafter, the learning engine operates to run the selected model on the training dataset to obtain a resulting output from the model. For example, in a preferred embodiment, the selected model is the multilayered, feed-forward neural networks, with a Tensor flow backend to build and train the neural networks.

The learning engine then selects and tunes other model arguments of the training dataset to establish an error percentage. Once the error percentage is (i.e., accuracy) established, the learning engine applies a ten-fold cross validation to establish a model stability of the selected model. Further, the learning engine operates dynamically by dynamically selecting the model arguments for each run of the selected model.

Further, the learning engine operates a final model run on the testing dataset to confirm the accuracy and/or fit of the selected model are within client acceptable limits. When the accuracy and/or fit of the selected model is not within the client acceptable limits or when there are more models left for consideration, a next model may be selected to begin the testing process over again. When the accuracy and/or fit of the selected model is determined to be within the client acceptable limits or when there are no more models left for consideration, selected model is established for use to predict health related emergency of the user of computing unit 110.

In certain other embodiments, the programming instructions may be based on any predetermined threat assessment model selected from a statistical models (e.g., linear regression, non-linear regression, Monte Carlo simulation), heuristic models (e.g., neural networks, fuzzy logic models, expert system models, state vector machine models useful in risk and safety prediction), and so on, that may be used to predict a possible health risk, well in advance.

In some embodiments, the back-end server 126 further includes a remedy determination module adapted to utilize the programming instruction set to generate a remedial plan adapted to reduce the chances of deteriorating the condition of the user. Further, such a threat rule set in accordance with remedial data-sets is adapted to provide a plurality of recommendations and/or lifestyle plans suitable for the user so as to overcome the impacts of the infection thereupon.

Program 128, having a set or multiple sets of program modules, may be stored in memory 120 and may include a health assessment program 130, and may also include additional programs 132, which may include, by way of example and not limitation, an operating system, one or more application programs, other program modules, and program data. Each of the operating system, one or more application programs, other program modules, and program data or some combination thereof, may include an implementation of a networking environment. Program/utility 128 generally carry out the functions and/or methodologies of embodiments described herein, and particularly a health assessment program 130 may carry out some or all of the functions and processes of embodiments described herein. In embodiments, one or more program 128, and potentially health assessment program 130, may store one or more data-sets for physical or physiological parameters related to an individual; the one or more program 128, including health assessment program 130, may be configured to permit one or more other program 128 and health assessment program 130 to access and/or update the one or more data-sets.

Computer system 110 may also communicate with one or more other internal devices or software systems, such as a Global Positioning System (GPS) 140. Computer system 110 may also communicate with one or more external devices 150 such as a keyboard, a pointing device, a display 160, etc.; one or more devices that enable a user to interact with computer system 110; and/or any devices (e.g., network card, modem, etc.) that enable computer system 110 to communicate with one or more other computing devices. Such communication can occur via Input/Output (I/O)) interfaces 114. Computer system 110 may also communicate with one or more networks such as a local area network (LAN), a general wide area network (WAN), a public network (e.g., the Internet), a cloud computing system or cloud computing node, and/or other networks via network adapter 116. As depicted, network adapter 116 communicates with the other components of computer system 110 via bus 118. It should be understood that although not shown, other hardware and/or software components could be used in conjunction with computer system 110. Examples, include, but are not limited to: microcode, device drivers, redundant processing units, external disk drive arrays, RAID systems, tape drives, and data archival storage systems, etc.

In embodiments, computer system 110 may also communicate with one or more sensors 170. The one or more sensors 170 may include a medical sensor 172, an environmental sensor 174, and may include other sensors 176. Other sensors 176 may include additional medical sensors, environmental sensors, and/or other types of sensors. Any one or more of the one or more sensors 170 may be external devices connected to or in communication with computer 110. Any one or more of the one or more sensors 170 may be integrated with computer system 110, whether as internally integrated devices or externally integrated devices, A medical sensor 172 may be a medical sensor configured to sense and collect data-sets pertaining to one or more physical or physiological parameters of an individual. By way of example only and not limitation, medical sensor 172 may be configured to sense a heart-rate, a respiratory rate, a blood pressure, an oxygen saturation level, a blood sugar level, a temperature, fertility, a ketone level, physical activity data, heart rate, HR variability, respiratory rate, biosensor data, cognitive data, pulse rate, galvanic skin response, and other specific indicators of chronic/cardiological symptoms (e.g. cough, changes in the user's voice, breathe sensors, behavior pattern, and the like), or other physical or physiological parameter. An environmental sensor 174 may be an environmental sensor configured to sense and collect data-sets pertaining to one or more environmental conditions pertaining to a location of an individual. By way of example only and not limitation, environmental sensor 174 may be configured to sense an external temperature, an internal temperature, an oxygen level, humidity, barometric pressure, noise, air speed, or other environmental parameter and using sensors such as high-resolution complementary metal-oxide semiconductor (CMOS) image sensor, global positioning system (GPS) sensor, accelerometer, gyroscope, magnetometer, ambient light sensor and microphone.

Figure 2:
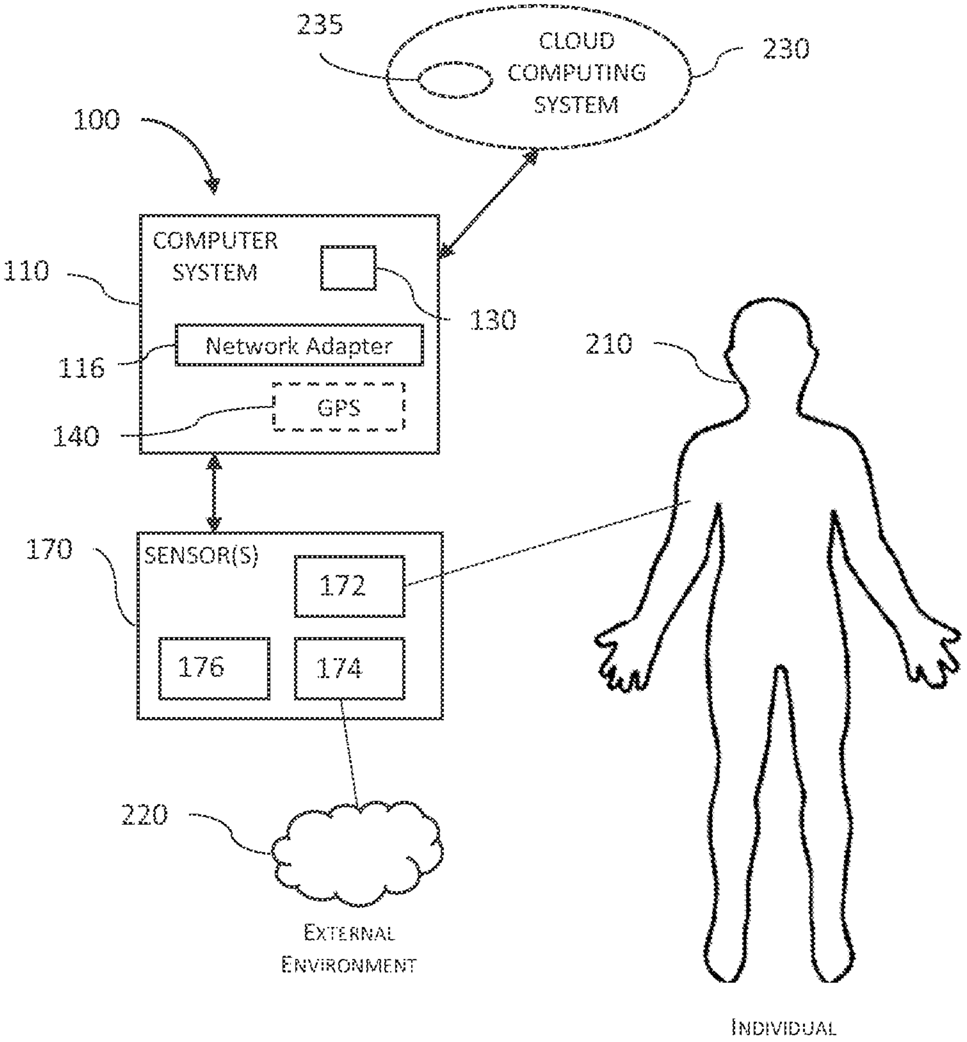
FIG. 2 depicts the system of FIG. 1 with additional components, in accordance with one or more embodiments set forth herein.

FIG. 2 depicts one or more embodiments of the system 100 of FIG. 1 in which computer system 110 (shown in FIG. 2 with only some of the components described in FIG. 1 for ease of understanding) is connected to or in communication with sensors 170, which may include, at least one medical sensor 172, at least one environmental sensor 174, and may include one or more other sensors 176. In embodiments as depicted by FIG. 2, computer system 110 and sensors 170 may be nearby or in proximity to an individual 210, such that medical sensor 172 may be operatively connected to the individual 210 in order to sense and collect the one or more data-sets pertaining to the one or more physical or physiological parameters of the individual 210. In one example embodiment, the medical sensor 172 may be a pulse oximeter configured to collect data-sets pertaining to an oxygen saturation level of the individual 210, and may be operatively connected to the individual 210 by a pulse oximeter by being placed and clipped to a finger of the individual 210. In another example embodiment, medical sensor 172 may be a blood-pressure device for measuring the blood pressure of individual 210, and may be connected to the individual 210 by a cuff placed on or around a wrist or arm of the individual 210.

In exemplary embodiments, environmental sensor 174 may sense and collect data-sets for the one or more environmental conditions by sensing environmental parameters nearby or in proximity to the individual in order to sense environmental conditions related to the location of individual 210. By way of example and not limitation, in embodiments environmental sensor 174 may be or may include a thermometer to sense an external temperature around environmental sensor 174, and thus sense the temperature around the location of individual 210. In another exemplary embodiment, environmental sensor 174 may be or may include a hygrometer to sense an external humidity around environmental sensor 174, and thus sense the humidity around the location of individual 210.

In some embodiments, computer system 110 may also be in communication with a cloud computing system 230 which may include one or more cloud computing nodes 235. As described in greater detail above in FIG. 1, computer system 110 may be operatively connected to or in communication with cloud computing system 230 and one or more cloud computing nodes 235 via one or more network adapters 116. As also described above in FIG. 1, computer system 110 may include a GPS system 140, which may also be connected to or in communication with cloud computing system 230 and one or more cloud computing nodes 235 via one or more network adapters 116. In exemplary embodiments, a location of computer system 110, and by extension a location of individual 210, may be obtained via GPS system 140 communicating through cloud computing system 230, which may in turn communicate with one or more satellites (not depicted in FIG. 2) to obtain the location of the computer system 110, and thus by extension the location of individual 210. Computer system 110, through one or more program 128, may then use the obtained location of computer system 110 to further obtain, through cloud computing system 230 and one or more cloud computing node 235, one or more environmental data-sets associated with the location of individual 210, such as a high altitude place, heavy traffic area, polluted cities, and the like. The one or more environmental data-sets obtained via cloud computing system 230 may be stored on any one or more computer system or server acting as a cloud computing node 235 in cloud computing system 230, and may be transmitted to computer system 110.

As an example of present invention, in an embodiment, a customized deep neural network (DNN) models that take in a location information of each of the plurality of users of the facility along with one or more infection related information from within the facility and/or out of the facility. Various factors relevant in estimating/predicting infection threats to one or more users of the facility are generally those which are known in the art to play a crucial role in predictions of spread of infection, especially in the areas of: (i) health (e.g., "health compared to others", "current opinion about health", "shortness of breath during a little physical activity such as walking up a slight hill"), (ii) personality traits (e.g., "consciousness as a personality trait", "agency as a personality trait"), (iii) personal beliefs (e.g., "live for today", "positive reappraisal", "lower aspirations"), (iv) well-being (e.g., "satisfied with life"), and, (v) demographic factors (e.g., "age"). The list of features as disclosed above is non-exclusive and may be formulated by the health professionals/researchers etc. in accordance with their knowledge and experience without deviating from the scope of the current disclosure.

The system 100 of the present subject matter is primarily utilized for assessing various environmental factors around a user of the computing device 110 to analyze and/or determine a state of emergency particularly, related to one or more chronic diseases such as heart attack, lung related disease, and/or other environmental effected diseases known in the art.

Further, the system 100 is configured to provide various health plans/recommendations/protocols to overcome such infections and/or disease. Various diseases and/or conditions may include but is not limited to Medically complex/chronic diseases such as COPD, Asthma, Cardiovascular diseases such as CHF, Valve disorders, HTN, and the like, Kidney Disease such as Chronic Renal Failure, Polycystic Kidney disease, Neurological/autoimmune conditions such as Multiple Sclerosis, Amyotrophic Lateral Sclerosis, Lupus, Sjorgen's Syndrome, Raynaud's Disease, Congenital Heart & Lung Defects in newborns, pregnancy and other health condition that may remotely be effected/impacted due to environmental conditions.

Further, the system 100 of the present invention provides an effective way of continuously assessing/monitoring health of a patient in real time. Advantageously, such an accurate and timely assessment of health condition of a patient is particularly beneficial in avoiding the unwanted emergency situations. Further, the system 100 is able to generate a visual alarm and audible alarm are in case of an anomaly in accordance with health assessment rules. Further, the back-end server 126 of the system 100 may be used to store medical histories of the patients. These records can be used to correlate the currently sensed data received from the sensors 170 for diagnosis. This pattern recognition process plays a pivotal role in the services mentioned subsequently. Further, emergency response is greatly improved using the system 100 of the current disclosure. For example, in case of a Level III emergency, a message/alarm is sent with vital parameters and threshold breaches only to the caregivers. For a Level II emergency, a message/alarm is sent in a similar manner but to both the patient's doctors and caregivers. For a Level I Emergency or emergency with the maximum threat, the system sends a call with a recorded message of the threat and breached parameters to both doctors and caregivers. Based on these alerts the patient is immediately attended by the doctors or the caregivers in an attempt to bring the patient back to a normal state with required treatment and medication.

Cloud computing is a model of service delivery for enabling convenient, on-demand network access to a shared pool of configurable computing resources (e.g. networks, network bandwidth, servers, processing, memory, storage, applications, artificial intelligence or machine learning applications, virtual machines, and services) that can be rapidly provisioned and released with minimal management effort or interaction with a provider of the service. This cloud model may include at least five characteristics, at least three service models, and at least four deployment models.

Characteristics of a cloud computing system may include:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models for a cloud computing system may include:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models for a cloud computing system may include:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. Cloud computing may utilize an infrastructure comprising a network of interconnected nodes. As described herein, a cloud computing system 230 may include one or more artificial intelligence applications or machine learning applications, as described herein elsewhere, that are stored on one or more of the one or more cloud computing nodes 235.

Referring again to FIG. 2, one or more physical or physiological parameters associated with individual 210 may be collected via medical sensor 172 and/or may be collected from the memory or storage system of system 100 and/or may be collected from a cloud computing system 230 via one or more cloud computing nodes 235; the one or more physical or physiological parameters may be communicated to health assessment program 130 of computer system 110. As well, one or more environmental parameters associated with a location of individual 210, obtained via environmental sensor 174 or from cloud computing system 230 (or both in some embodiments) may be communicated to health assessment program 130 of computer system 110. As further described below and in connection with FIG. 3, health assessment program 130 uses the environmental parameters and data in conjunction with the physical or physiological parameters and data to generate a health threat assessment that may be output to individual 210.

Figure 3:
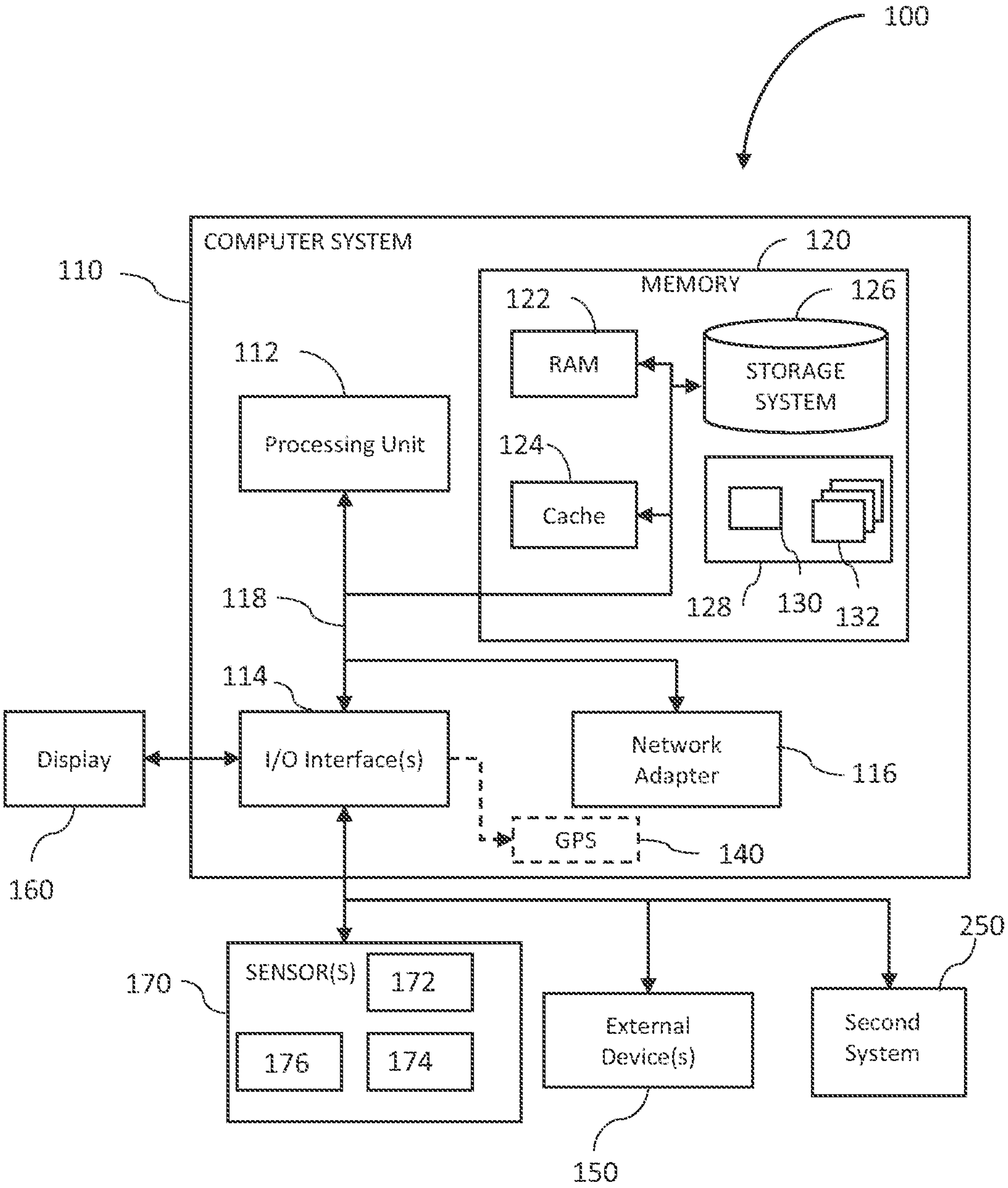
FIG. 3 depicts the system of FIG. 1 with additional components, in accordance with one or more embodiments set forth herein.

FIG. 3 depicts another embodiment of system 100, in which the computer system 110 of system 100 may be a first computer system, and the system may further include a second computer system 250. The second computer system 250 may be in communication with the first computer system 110, and may be any kind of system or device that can be configured to communicate with the first computer system 110, such as a personal computer system, server computer system, thin client, thick client, hand-held or laptop device, multiprocessor system, microprocessor-based system, set top box, mobile device such as a mobile phone or tablet, programmable consumer electronics, network PC, minicomputer system, mainframe computer system, and distributed cloud computing environment and/or cloud computing node that include any of the above systems or devices, and the like. As described further herein, in exemplary embodiments second computer system 250 may be a second output device configured to output a health threat assessment in readable format to an individual. In some embodiments, first computer system 110 may be a first output device used by an individual that the individual uses to receive health threat assessments, as described above herein; second computer system 250 may be a second output device used by another person to receive health threat assessments generated for the individual. The other person may be any person but typically may be another person with a need to know when health threat assessments have been generated for the individual, such as a family member assisting with medical care of the individual, a health-care professional monitoring the individual's medical condition, and the like.

Figure 4:
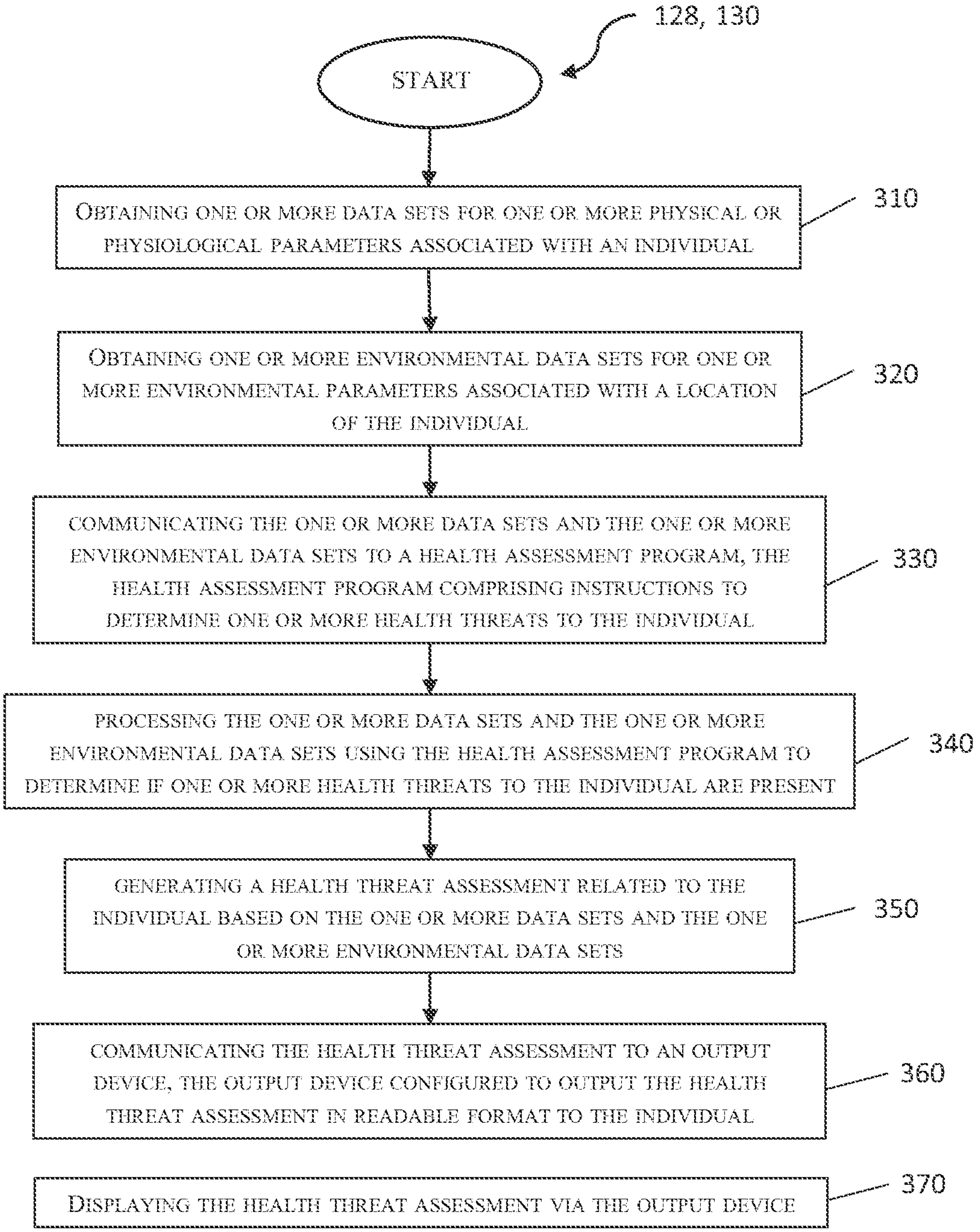
FIG. 4 depicts, in block format, a workflow for one or more processes, in accordance with one or more embodiments set forth herein.

FIG. 4 depicts, in block format, a workflow in accordance with one or more embodiments set forth herein. By way of example, the processes described with respect to FIG. 4 may be performed using one or more program 128, including health assessment program(s) 130, on one or more systems 100 as described herein.

In the embodiment of FIG. 4, one or more program 128 at block 310 obtains one or more data-sets for one or more physical or physiological parameters associated with an individual. By way of example only and not limitation, the one or more data-sets may relate to physical or physiological parameters for a heart-rate, a respiratory rate, a blood pressure, an oxygen saturation level, a blood sugar level, a temperature, fertility, a ketone level, or other physical or physiological parameter. The one or more data-sets may, in embodiments, be obtained using one or more medical sensors. The one or more data-sets may, in embodiments, be obtained from a storage system or memory of a computer system, as described in more detail in FIGS. 1-3. As an example of the workflow of FIG. 4 in practical operation, the program 128 may retrieve data-sets for an individual's blood pressure. The data-sets may be retrieved from a storage system or memory of a computer system, or may be stored as part of program 128 or health assessment program 130 as described herein. Program 128 may also or alternatively use a medical sensor, such as a blood pressure monitor, to sense and collect data-sets pertaining to the individual's blood pressure at a particular moment or continuously in real-time.

At block 320, one or more program 128 obtains one or more environmental data-sets for one or more environmental parameters associated with a location of the individual. By way of example only and not limitation, the one or more environmental data-sets may relate to environmental parameters for an external temperature, an internal temperature, an oxygen level, humidity, barometric pressure, or other environmental parameter. The environmental data-sets may be obtained using one or more environmental sensors, may be obtained by retrieving the environmental data-sets from a cloud computing node or other system, or may be obtained using both one or more environmental sensors and by retrieving environmental data-sets from a cloud computing node. Continuing the example from above, the program 128 may obtain environmental data-sets pertaining to temperature parameters for the individual's location by way of a thermometer.

At block 330, the one or more data-sets obtained at block 310 and the one or more environmental data-sets obtained at block 320 are communicated to the health assessment program. The health assessment program may be the health assessment program 130 depicted in FIGS. 1-3. The health assessment program may include instructions to determine one or more health threats to an individual. Continuing again the example from above, the process communicates the blood pressure data-sets for the individual and the temperature data-sets, obtained at blocks 310 and 320 respectively, to the health assessment program.

At block 340, the health assessment program processes the one or more data-sets and the one or more environmental data-sets to determine if one or more health threats to the individual are present. The health threat may be an immediate or imminent health threat that requires immediate treatment or remedy, or it may be a future health threat that may be remedied before becoming an immediate health threat. The processing may be any set of instructions for combining or correlating the one or more data-sets with the one or more environmental data-sets in order to determine if a health threat exists or potentially will exist for the individual. By way of example, the health assessment program may correlate the one or more data-sets with the environmental data-sets through a look-up table, which may then inform the health assessment program of an existing health threat dependent on a result obtained from the look-up table. By way of another example, the health assessment program may include instructions for performing one or more algorithms to process the one or more data-sets and the environmental data-sets to determine if a health threat exists for the individual. Other processes or methods for processing one or more data-sets and one or more environmental data-sets are possible and contemplated within the scope of this disclosure. Continuing the example from above, the health assessment program may correlate the temperature data-sets related to the individual's location with the blood-pressure data-sets related to the individual through a look-up table that informs the health assessment program of what temperature or temperature range(s) pose health threats to the individual with a high blood pressure. The health assessment program may use blood pressure data-sets obtained by a blood pressure monitoring device used or worn by the individual, where the device is configured to sense the individual's blood pressure at a particular moment or to continuously monitor the individual's blood pressure. The health assessment program may, alternatively or additionally, use blood pressure data-sets for the individual that have been stored in a storage system or computer system memory, as described elsewhere herein.

At block 350, the one or more program 128 generates a health threat assessment related to the individual that is based on the one or more data-sets and the one or more environmental data-sets. Generation of the health threat assessment may be accomplished by any set of program instructions and may generate the health threat assessment in any form or format appropriate for the particular computer system or systems on or through which the health assessment program is being used. The health threat assessment generated may, in some embodiments, be a simple binary determination that a health threat does or does not exist for the individual. In other embodiments, the health threat assessment may be a robust or detailed analysis of the type or degree of health threat that exists for the individual, including detail on how serious the health threat is, what further health risks may arise if remedial actions are not taken, and so on. Other examples of health threat assessments are possible and contemplated within the scope of the present disclosures. Continuing the previous example, after correlating the sensed temperature with the individual's blood-pressure data, the health assessment program may determine that a serious health threat exists for the individual because the high temperature parameters detected correlate to increased risk of heart attack for the individual with high blood pressure, and the health assessment program consequently generates a health threat assessment detailing the severity of the health threat and risks to the individual.

At block 360, the health threat assessment is communicated to an output device, with the output device being configured to output the health threat assessment in readable format to the individual, and, at block 370, the health threat assessment is displayed via the output device. As described herein elsewhere, the output device may be any output device capable of displaying a health threat assessment in a format that the individual can read or view, or the output device may be capable of being configured or programmed to perform the function of displaying the health threat assessment in readable format. In exemplary embodiments the output device may be a mobile device, such as a mobile phone or tablet, that the individual uses and may access. In other embodiments the output device may be a desktop computer or laptop computer. In still other embodiments the output device may be a dedicated device that is configured for the purpose of displaying the health threat assessment. As already detailed elsewhere, numerous other output devices are possible and contemplated within the scope of the present disclosures. Continuing and completing the example scenario from above, the health threat assessment may be put into a readable format, such as a visual report or a text-based read-out, and displayed on the individual's mobile phone. The health threat assessment may be displayed automatically upon generation, or may be displayed upon the individual opening a particular program or application that is used for viewing or reading the health threat assessments.

Figure 5:
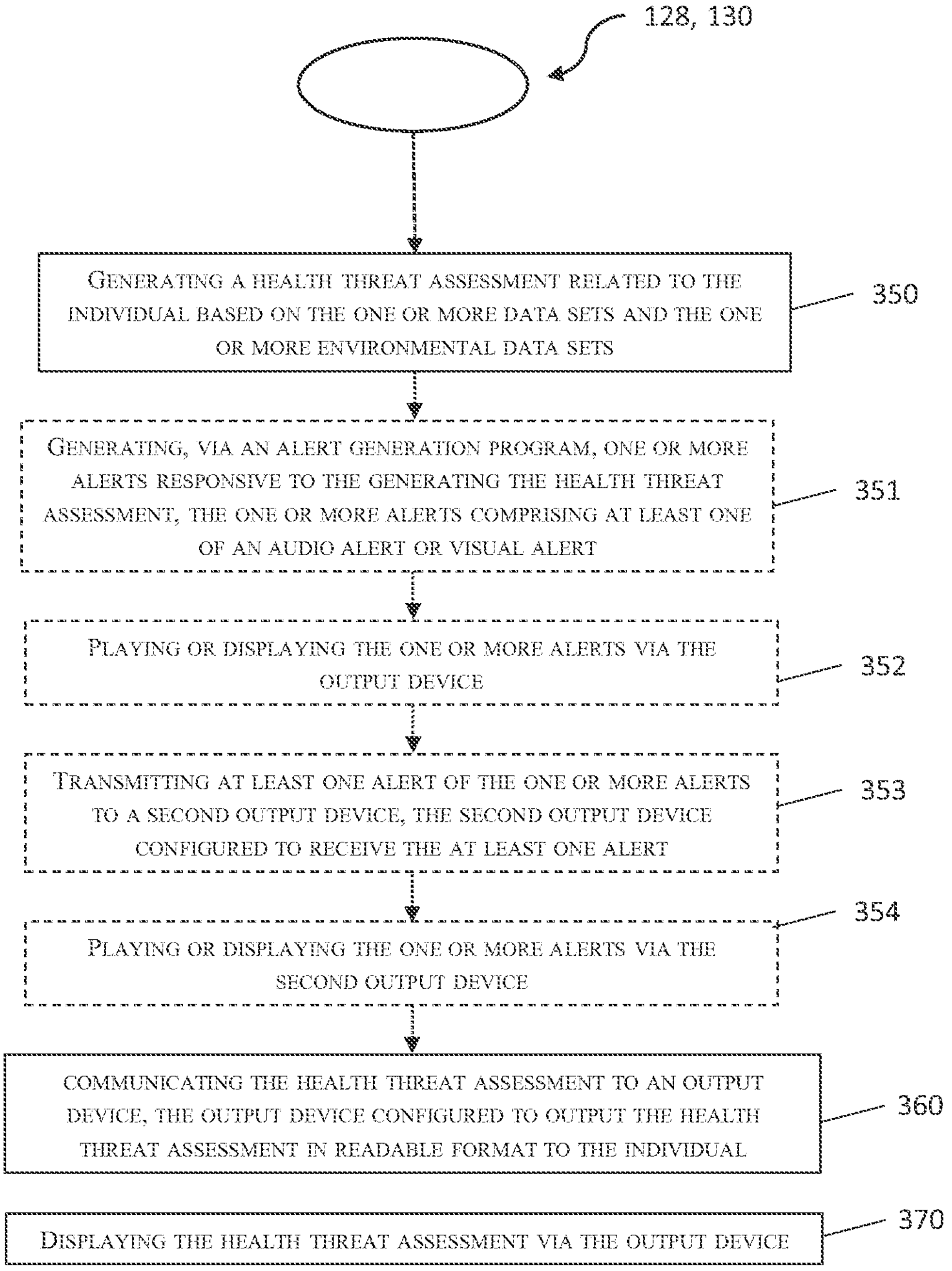
FIG. 5 depicts additional embodiments of steps of the processes of FIG. 4, in accordance with one or more embodiments set forth herein.

FIG. 5 depicts one or more additional embodiments of the processes depicted and described in FIG. 4, with additional optional steps shown in block format within a portion of the processes of FIG. 4 and other steps of the process not depicted in FIG. 5 for ease of understanding. At block 351, one or more program 128, 130 may, responsive to generating the health threat assessment, generate one or more alerts via an alert generation program. The alert generation program may be one program or multiple programs of the one or more programs 128; in some embodiments the alert generation program may be part of or integrated with the health assessment program 130. In exemplary embodiments the alert generated is at least one of an audio or visual alert. An audio alert may be, for example, a sound or tone that can be played and that is associated with the generation of the health threat assessment. A visual alert may be, for example, a text message or e-mail notification that can be displayed and that is associated with the generation of the health assessment. At block 352, the alert is played or displayed, depending on the type of alert generated, on the output device. In embodiments in which the health threat assessment is to be accessed via the individual opening an application or program on the output device, an audio or visual alert may be useful for notifying the individual that the health threat assessment has been generated and may prompt the individual to view the health threat assessment.

Additional steps may also be part of the process depicted in FIG. 5. The output device may be, for example, a first output device, and a second output device may also be available as part of the system and process. The second output device may be any computer system, mobile device such as a mobile phone or tablet, laptop system, or other system as already described herein. The alert or alerts generated at block 351 may further, at block 353, be transmitted to the second output device, and at block 354 the alert or alerts are played or displayed via the second output device. Transmitting the alert(s) to a second output device may, in some embodiments, allow another person to receive alerts related to the individual so that person may know of and potentially read or view the health threat assessments associated with that individual. This may permit family members, caretakers, health-care professionals, or other persons to know when a health threat is present for the individual concerned. In other embodiments, the second output device may be another device used by the individual, so that the individual may receive notification of health threat assessments that have been generated and made available on another first output device.

Figure 6A:
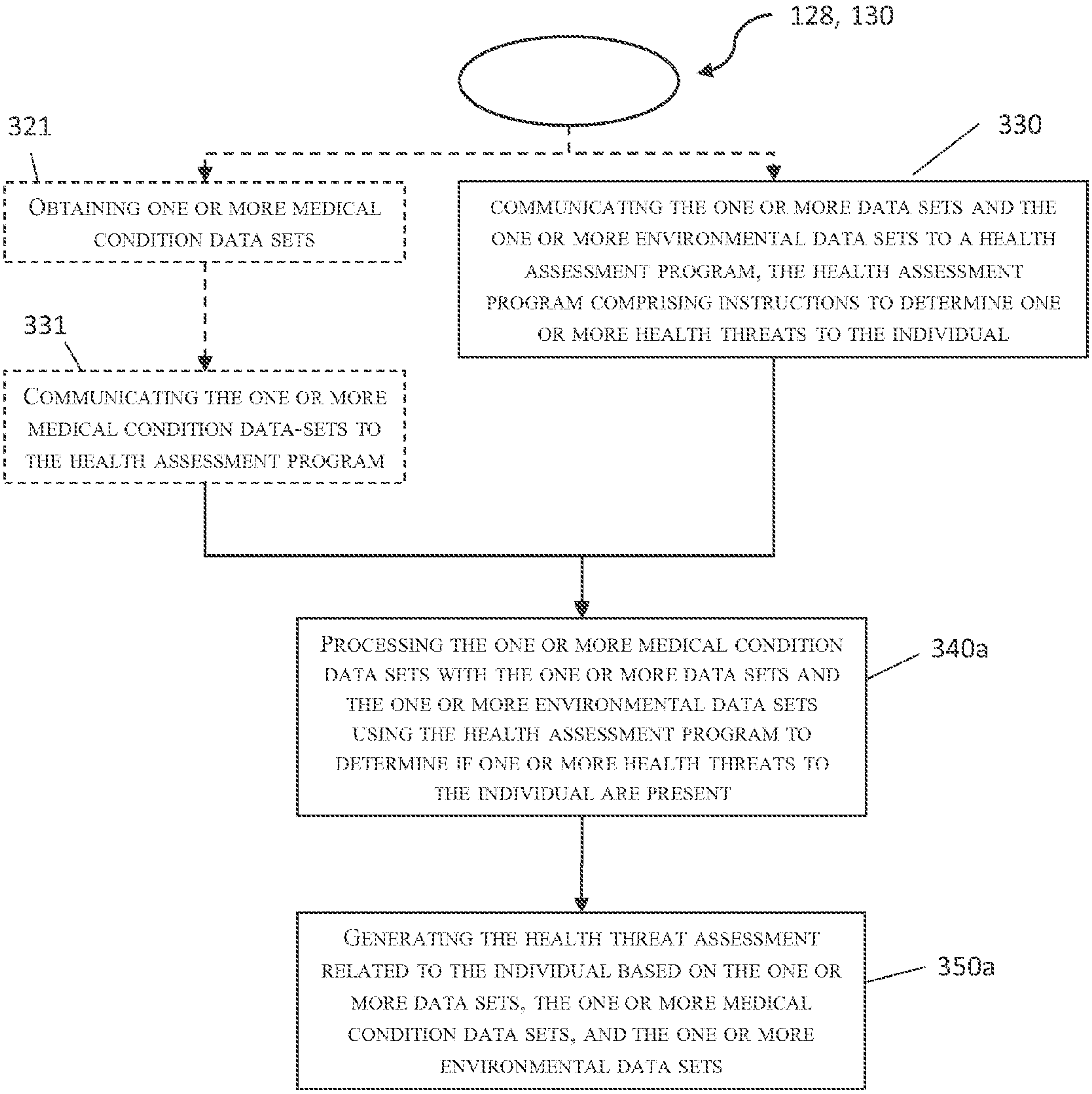
FIG. 6A depicts additional embodiments of steps of the processes of FIG. 4, in accordance with one or more embodiments set forth herein.

FIG. 6A depicts one or more additional embodiments of the processes depicted and described in FIG. 4, with additional optional steps shown in block format within a portion of the processes of FIG. 4 and other steps of the process not depicted in FIG. 6 for ease of understanding. In the processes depicted in FIG. 6, an additional optional step 321 may include obtaining one or more medical condition data-sets. The one or more medical condition data-sets may include data for, by way of example only, one or more of: a medical history of the individual; medical records of the individual; a medical condition or disease pertaining to the individual; information regarding remedial care for a medical condition or disease pertaining to the individual. Other medical condition data-sets may also be included in the one or more medical condition data-sets.

At block 331, the process may take the additional optional step of communicating the one or more medical condition data-sets to the health assessment program. Communicating the one or more medical condition data-sets to the health assessment program may be accomplished in the same way or a similar way to communicating the one or more data-sets and/or the one or more environmental data-sets to the health assessment program, or may be accomplished by any other means.

FIG. 6A further depicts, at block 340*a*, a modified version of step 340 of FIG. 4; at block 340*a* the process further includes processing the one or more medical condition data-sets with the one or more data-sets and the one or more environmental data-sets using the health assessment program to determine if one or more health threats to the individual are present. Finally, at block 350*a*, a modified version of step 350 of FIG. 4, the process generates the health threat assessment related to the individual based on the one or more data-sets, the one or more medical condition data-sets, and the one or more environmental data-sets.

Figure 6B:
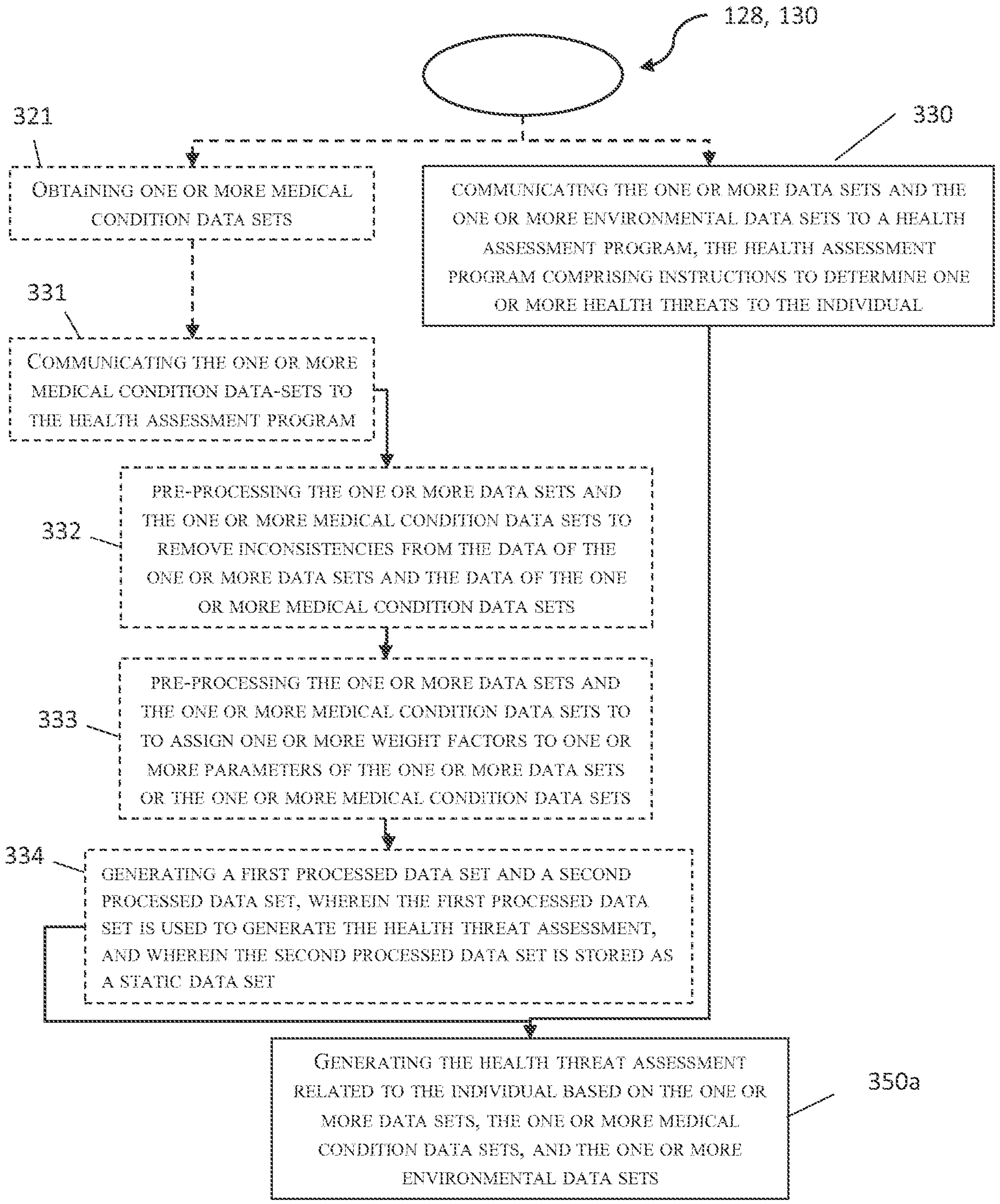
FIG. 6B depicts additional embodiments and steps of the processes of FIG. 6A, in accordance with one or more embodiments set forth herein.

FIG. 6B depicts additional steps of the process depicted in FIG. 6A that may optionally be taken. Prior to processing the one or more data-sets, the one or more environmental data-sets, and the one or more medical condition data-sets, the process may include one or more pre-processing steps that remove inconsistencies from data-sets and/or assign weights or weighting factors to one or more parameters of the one or more data-sets. Pre-processing steps may be performed, for example, by an artificial intelligence application or machine learning application as described elsewhere herein. An artificial intelligence application or machine learning application may be embodied in the one or more program 128 or may be part of the health assessment program 130. Pre-processing steps may be carried out on system 100 or may be carried out on another system, such as a cloud computing node 235 of a cloud computing system 230, that is operatively connected with the system 100. The process may, at block 332, perform pre-processing of the one or more data-sets and the one or more medical condition data-sets to remove inconsistencies from the data of the one or more data-sets and the data of the one or more medical condition data-sets. At block 333, the process may perform pre-processing of the one or more data-sets and the one or more medical condition data-sets to assign one or more weight factors to one or more parameters of the one or more data-sets or the one or more medical condition data-sets. At block 334, the process may, prior to generating the health threat assessment, perform generating a first processed data-set and a second processed data-set. The first processed data-set may be used to generate the health threat assessment, as described above. The second processed data-set may be stored as a static data-set. The static data-set may, for example, be used as a data-set for testing purposes or training purposes, or for any other purpose where data-sets are needed for any other process that would otherwise modify, overwrite, or destroy the data of the first data-set. By generating a first processed data-set and a second processed data-set, or even additional processed data-sets after the first and second, health threat assessment data-sets may be used for a primary purpose of alerting or informing an individual of immediate or near-future health threats while the additional data-set(s) may be used separately and independently of the first processed data-set for further analysis, reporting, testing, training, or other purpose.

The systems and processes described herein have been described in the context of systems and processes for obtaining data-sets and environmental data-sets related to an individual, processing the data-sets and environmental data-sets to generate a health threat assessment for that individual, and outputting the health threat assessment to an output device for the benefit of the individual or other persons with an interest in potential health threats to that individual. Such systems and processes may be integrated into and be part of larger systems and processes for collecting and analyzing health threat data for multiple individuals or large populations of individuals. Such systems and processes may include one or more artificial intelligence applications or machine learning applications, as described herein, that have been configured, at least in part, to perform the processes of collecting and analyzing health threat data for multiple individuals or large populations of individuals. As described above in conjunction with FIGS. 6A and 6B, the systems and processes described may generate partitioned data-sets in the form of a first processed data-set and a second processed data-set (or one or more second data-sets). The first processed data-set may be used, as described herein, to generate health threat assessments for a single individual. The second processed data-set(s) may be used for the purposes of analyzing health threats to several individuals or entire populations of individuals with the same or similar health conditions. The second processed data-set(s) may be communicated to a computer program, which may one program of the one or more programs 128 stored in another part of system 100 of FIGS. 1-3, or which may be stored on another system separate from system 100, such as a cloud computing node 235 of a cloud computing system 230 as depicted in FIG. 2. The second processed data-set(s) generated for one individual may be stored with other processed data-set(s) pertaining to other individuals, forming a set or collection of processed data-sets containing data and data-sets from multiple individuals. At any time, using one or more program 128 of system 100 or using any program or programs of any other system, the collection of processed data-sets may be used to generate analyses, statistics, charts, tables, or any other reports pertaining to one or more health threats to a population of individuals that share the same or similar health conditions and who may live in the same or similar location and environment(s) as other individuals with those health conditions. These analyses or other reports may assist scientists, health-care professionals, and others in understanding the health risks to individuals with certain health conditions in certain environments, and use that understanding to further refine remedies, protocols, or treatments responsive to those health conditions.

As described above, an artificial intelligence application or machine learning application may be one or more of the programs 128, and may also be part of the health assessment program 130. An artificial intelligence application or machine learning application may also be one of or a part of any number of programs stored on any other system that can be operatively connected with system 100 of FIG. 1, such as a cloud computing node 235 of a cloud computing system 230, or a separate system that can connect with or communicate with a cloud computing system 230 or any other network of computing systems. Any one or more of the steps depicted in FIGS. 6A and 6B may, in exemplary embodiments, be performed via an artificial intelligence application or machine learning application. Use of an artificial intelligence application or machine learning application to perform pre-processing of data-sets, for example, may allow such application to iteratively develop better and more accurate or refined pre-processing algorithms, which may then be used for pre-processing of one or more next data-sets that must be collected and analyzed. In other embodiments, an artificial intelligence application or machine learning application may be used to analyze and generate reports based on data-sets, such as the second data-set and additional second data-sets as described in FIG. 6A-B, so that each data-set used in analysis and reporting may subsequently inform the artificial intelligence application or machine learning application and allow it to improve or refine the analysis and reporting algorithms themselves.

Approximating language, as used herein throughout the specification and claims, may be applied to modify any quantitative representation that could permissibly vary without resulting in a change in the basic function to which it is related. Accordingly, a value modified by a term or terms, such as “about,” is not limited to the precise value specified. In some instances, the approximating language may correspond to the precision of an instrument for measuring the value.

The terminology used herein is for the purpose of describing particular examples only and is not intended to be limiting of the disclosure. As used herein, the singular forms “a”, “an” and “the” are intended to include the plural forms as well, unless the context clearly indicates otherwise. It will be further understood that the terms “comprise” (and any form of comprise, such as “comprises” and “comprising”), “have” (and any form of have, such as “has” and “having”), “include” (and any form of include, such as “includes” and “including”), and “contain” (and any form of contain, such as “contains” and “containing”) are open-ended linking verbs. As a result, a method or device that “comprises,” “has,” “includes” or “contains” one or more steps or elements possesses those one or more steps or elements, but is not limited to possessing only those one or more steps or elements. Likewise, a step of a method or an element of a device that “comprises,” “has,” “includes” or “contains” one or more features possesses those one or more features, but is not limited to possessing only those one or more features.

As used herein, the terms “may” and “may be” indicate a possibility of an occurrence within a set of circumstances; a possession of a specified property, characteristic or function; and/or qualify another verb by expressing one or more of an ability, capability, or possibility associated with the qualified verb. Accordingly, usage of “may” and “may be” indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

While several aspects have been described and depicted as set forth herein, alternative aspects may be effected by those skilled in the art to accomplish the same objectives. Accordingly, it is intended by the appended claims to cover all such alternative aspects as fall within the true spirit and scope of the disclosure.

What is claimed is:

1. A method comprising:

providing a health assessment program executed by a processor of a computing device, the computing device in communication with a cloud computing system having at least one cloud computing node, wherein at least one network adapter is connected between the at least one cloud computing node and the computing device;

obtaining, by the computing device, one or more data-sets for one or more physical or physiological parameters associated with an individual using at least one medical sensor carried by the individual, the at least one medical sensor in communication with the computing device, and capable of sensing in real time at least one of: a heart-rate; a respiratory rate; a blood pressure; an oxygen saturation level; a blood sugar level; a temperature; fertility; a ketone level; a physical activity level; a heart rate variability; a galvanic skin response; a cough; a change in a voice; or a behavior pattern;

obtaining, by the computing device, one or more environmental data-sets for one or more environmental parameters associated with a location of the individual, wherein the computing device uses the health assessment program and a location of the computing device to obtain, through the cloud computing system and the at least one cloud computing node, the one or more environmental data-sets associated with the location of the individual, wherein the one or more environmental data-sets is at least one of: a pollen count; an external temperature; an internal temperature; an oxygen level; humidity; barometric pressure; noise; air speed; acceleration; ambient light; altitude; traffic; or pollution;

storing the one or more data-sets and the one or more environmental data sets in a shared storage data hub;

training a machine learning algorithm to generate a health threat assessment, wherein training comprises:

collecting the one or more data-sets and the one or more environmental data-sets from the shared storage data hub;

applying one or more pre-processes to each data-set to remove inconsistencies from the one or more data-sets and to assign a weight to each parameter of the one or more data-sets;

creating a training set comprising a partition of the one or more pre-processed data-sets, wherein the partition of the one or more pre-processed data-sets comprises:

a first processed data-set and a second processed data set, wherein the first processed data-set and the second processed data-set are generated prior to generating the health threat assessment, wherein the first processed data-set is used to generate the health threat assessment, and wherein the second processed data-set is separately stored as a static data-set to test and train the machine learning algorithm, and wherein the second processed data-set is used to modify, overwrite, or destroy data of the first processed data-set;

generating a learning model by dynamically selecting weights and parameters of the one or more data-sets;

training a neural network using the training set; and establishing an accuracy level of the learning model using the training set;

communicating the one or more data-sets and the one or more environmental data-sets to the health assessment program executed by the processor of the computing device, the health assessment program comprising instructions to determine one or more health threats to the individual, and wherein the instructions of the health assessment program use a determination from the neural network after training;

processing, with the processor, the one or more data-sets and the one or more environmental data-sets using the health assessment program to determine if one or more health threats to the individual are present in real time;

generating a health threat assessment related to the individual based on the one or more data-sets and the one or more environmental data-sets;

communicating one or more alerts of the health threat assessment to an electronic output device associated with the individual, the electronic output device configured to output the one or more alerts of the health threat assessment in readable format to the individual;

displaying the one or more alerts of the health threat assessment on the output device; and providing the individual with additional information related to or generated by the health threat assessment.

2. The method of claim 1, wherein obtaining one or more environmental data-sets further comprises obtaining, via one or more environmental sensors, the one or more environmental data-sets associated with the location of the individual.

3. The method of claim 1, further comprising:

an alert generation program generating the one or more alerts of the health threat assessment responsive to generating the health threat assessment, the one or more alerts comprising at least one of an audio alert or visual alert; and wherein displaying the one or more alerts comprises playing or displaying the one or more alerts via the output device.

4. The method of claim 3, wherein the output device is a first output device, and further comprising:

transmitting at least one alert of the one or more alerts to a second output device, the second output device configured to receive the at least one alert; and playing or displaying the at least one alert via the second output device.

5. The method of claim 1, further comprising:

obtaining one or more medical condition data-sets;

communicating the one or more medical condition data-sets to the health assessment program;

processing the one or more medical condition data-sets with the one or more data-sets and the one or more environmental data-sets using the health assessment program to determine if one or more health threats to the individual are present; and, generating the health threat assessment related to the individual based on the one or more data-sets, the one or more medical condition data-sets, and the one or more environmental data-sets.

6. The method of claim 5, wherein the one or more medical condition data-sets includes data for one or more of the following: a medical history of the individual; medical records of the individual; a medical condition or disease pertaining to the individual; information regarding remedial care for a medical condition or disease pertaining to the individual.

7. The method of claim 5, further comprising, prior to processing the one or more medical condition data-sets with the one or more data-sets:

pre-processing the one or more data-sets and the one or more medical condition data-sets to remove inconsistencies from the data of the one or more data-sets and the data of the one or more medical condition data-sets;

pre-processing the one or more data-sets and the one or more medical condition data-sets to assign one or more weight factors to one or more parameters of the one or more data-sets or the one or more medical condition data-sets; and, prior to generating the health threat assessment, generating the first processed data-set and the second processed data-set.

8. The method of claim 1, further comprising:

communicating the second processed data-set to a computer program, the computer program configured to store the second processed data-set with one or more additional processed data-sets for other individuals; and, generating a report, based on the second processed data-set and the one or more additional processed data-sets, pertaining to one or more health threats to a population of individuals.

9. The method of claim 1, wherein additional information related to or generated by the health threat assessment is at least one of: a lifestyle plan; a remedial plan adapted to reduce chances of deteriorating condition of the individual; or recommendations to overcome impacts of infection.

10. A system comprising:

a computing device in communication with a cloud computing system having at least one cloud computing node, wherein at least one network adapter is connected between the at least one cloud computing node and the computing device, the computing device having:

a memory;

one or more processing apparatuses in communication with the memory;

a non-transitory computer readable storage medium; and one or more health assessment programs comprising program instructions stored on the non-transitory computer readable storage medium and executable by the one or more processing apparatus via the memory to perform a method, the method comprising:

obtaining, by the computing device, one or more data-sets for one or more physical or physiological parameters associated with an individual using at least one medical sensor carried by the individual, the at least one medical sensor in communication with the computing device, and capable of sensing in real time at least one of: a heart-rate; a respiratory rate; a blood pressure; an oxygen saturation level; a blood sugar level; a temperature; fertility; a ketone level; a physical activity level; a heart rate variability; a galvanic skin response; a cough; a change in a voice; or a behavior pattern;

obtaining, by the computing device, one or more environmental data-sets for one or more environmental parameters associated with a location of the individual, wherein the computing device uses the health assessment program and a location of the computing device to obtain, through the cloud computing system and the at least one cloud computing node, the one or more environmental data-sets associated with the location of the individual, wherein the one or more environmental data-sets is at least one of: a pollen count; an external temperature; an internal temperature; an oxygen level; humidity; barometric pressure; noise; air speed; acceleration; ambient light; altitude; traffic; or pollution;

storing the one or more data-sets and the one or more environmental data sets in a shared storage data hub;

training a machine learning algorithm to generate a health threat assessment, wherein training comprises:

collecting the one or more data-sets and the one or more environmental data-sets from the shared storage data hub;

applying one or more pre-processes to each data-set to remove inconsistencies from the one or more data-sets and to assign a weight to each parameter of the one or more data-sets;

creating a training set comprising a partition of the one or more pre-processed data-sets, wherein the partition of the one or more pre-processed data-sets comprises:

a first processed data-set and a second processed data set, wherein the first processed data-set and the second processed data-set are generated prior to generating the health threat assessment, wherein the first processed data-set is used to generate the health threat assessment, and wherein the second processed data-set is separately stored as a static data-set to test and train the machine learning algorithm, and wherein the second processed data-set is used to modify, overwrite, or destroy data of the first processed data-set;

generating a learning model by dynamically selecting weights and parameters of the one or more data-sets;

training a neural network using the training set;

establishing an accuracy level of the learning model using the training set;

communicating the one or more data-sets and the one or more environmental data-sets to the one or more health assessment programs, the one or more health assessment programs comprising instructions to determine one or more health threats to the individual, and wherein the instructions of the health assessment program use a determination from the neural network after training;

processing the one or more data-sets and the one or more environmental data-sets using the health assessment program to determine if one or more health threats to the individual are present in real time;

generating a health threat assessment related to the individual based on the one or more data-sets and the one or more environmental data-sets;

communicating one or more alerts of the health threat assessment to an electronic output device associated with the individual, the electronic output device configured to output the one or more alerts of the health threat assessment in readable format to the individual;

displaying the one or more alerts of the health threat assessment on the output device; and providing the individual with additional information related to or generated by the health threat assessment.

11. The system of claim 10, further comprising one or more environmental sensors in communication with the processing apparatus, and wherein obtaining one or more environmental data-sets further comprises obtaining, via the one or more environmental sensors, the one or more environmental data-sets associated with the location of the individual.

12. The system of claim 10, wherein the method further comprises:

an alert generation program generating the one or more alerts of the health threat assessment responsive to generating the health threat assessment, the one or more alerts comprising at least one of an audio alert or visual alert, and wherein displaying the one or more alerts comprises playing or displaying the one or more alerts via the output device.

13. The system of claim 12, wherein the output device is a first output device and further comprising a second output device, and wherein the method further comprises:

transmitting at least one alert of the one or more alerts to a second output device, the second output device configured to receive the at least one alert, and playing or displaying the at least one alert via the second output device.

14. The system of claim 10, wherein the one or more programs further comprises program instructions for:

obtaining one or more medical condition data-sets;

communicating the one or more medical condition data-sets to the health assessment program; and processing the one or more medical condition data-sets with the one or more data-sets to generate the health threat assessment.

15. The system of claim 14, wherein the one or more programs comprises a pre-processing program, and wherein prior to processing the one or more medical condition data-sets with the one or more data-sets the one or more programs further comprises program instructions for:

via the pre-processing program, pre-processing the one or more data-sets and the one or more medical condition data-sets to remove inconsistencies from the data of the one or more data-sets and the data of the one or more medical condition data-sets;

via the pre-processing program, pre-processing the one or more data-sets and the one or more medical condition data-sets to assign one or more weight factors to one or more parameters of the one or more data-sets or the one or more medical condition data-sets; and, prior to generating the health threat assessment, generating the first processed data-set and the second processed data-set.

16. The system of claim 10, wherein additional information related to or generated by the health threat assessment is at least one of: a lifestyle plan; a remedial plan adapted to reduce chances of deteriorating condition of the individual; or recommendations to overcome impacts of infection.

* * * * *